(12) United States Patent
Ito

(10) Patent No.: US 6,830,919 B1
(45) Date of Patent: Dec. 14, 2004

(54) CERAMIDASE GENE

(75) Inventor: Makoto Ito, Fukuoka (JP)

(73) Assignee: Takara Bio Inc., Otsu (JP)

(*) Notice: Subject to any disclaimer, the term of this patent is extended or adjusted under 35 U.S.C. 154(b) by 0 days.

(21) Appl. No.: 09/937,521

(22) PCT Filed: Mar. 24, 2000

(86) PCT No.: PCT/JP00/01802

§ 371 (c)(1),
(2), (4) Date: Sep. 26, 2001

(87) PCT Pub. No.: WO00/58448

PCT Pub. Date: Oct. 5, 2000

(30) Foreign Application Priority Data

Mar. 26, 1999 (JP) .......................................... 11-084743

(51) Int. Cl.$^7$ ............................. C12N 9/80; C07H 21/04
(52) U.S. Cl. ...................... 435/228; 435/227; 435/325; 435/252.33; 435/320.1; 536/23.2; 536/23.1; 536/23.5; 424/94.6
(58) Field of Search ................................ 435/228, 227, 435/325, 252.33, 320.1, 195, 252.3, 410; 536/23.1, 23.2, 23.5; 424/94.6

(56) References Cited

U.S. PATENT DOCUMENTS 6,258,581 B1 * 7/2001 Okino et al. ................ 535/195

FOREIGN PATENT DOCUMENTS

| JP | 05015370 | 1/1993 |
| JP | 05015371 | 1/1993 |
| JP | 10257884 | 9/1998 |

OTHER PUBLICATIONS

Marra et al. Data base: EST, Accession No. AA920146, Apr. 20, 1998.*
Spence et al., Biochemistry and Cell Biology, vol. 64, No. 5, 1986.
T.E. Creighton, The Amino Acid Sequence (pp. 31–42), in Proteins: Structures and Molecular Properties; W.H. Freeman and Company, New York, NY (2$^{nd}$ ed. 1993).
Motohiro Tani et al.; Journal of Biological Chemistry, vol. 275, No. 5, Feb. 4, 2000, pp. 3462–3468.
Yu–Wei Shen et al.; Investigative Ophthalmology & Visual Science, vol. 22, No. 6, 1982, pp. 734–743.
Jurgen Koch et al.; Journal of Biological Chemistry, vol. 271, No. 51, 1996, pp. 33110–33115.
IBM Technical Disclosure Bulletin; vol. 33, No. 5, p. 208, Oct. 1990.
Ake Nilsson et al.; Biochimica et Biophysica Acta, vol. 176, No. 2, 1969, pp. 339–347.
Emmanuel Coroneos et al.; Journal of Biological Chemistry, American Society of Biological Chemists, vol. 270, No. 40, Oct. 6, 1995, pp. 23305–23309.
Bawab, S. E. et al.: "Purification and characterization of a membrane–bound nonlysosomal ceramidase from rat brain", J. Biol. Chem. Sep., 1999, vol. 274, No. 39, pp. 27948–27955.
Tani, M. et al., "Specific and sensitive assay for alkaline and neutral ceramidases involving C12–NBD–ceramide", J. Biochem. (Apr., 1999), vol. 125, No. 4, pp. 746–749.
Yada, Y. et al., "Purification and biochemical characterization of membrane–bound epidermal ceramidases from guinea pig skin", J. Biol. Chem. (1995), vol. 270, No. 21, pp. 12677–12684.
Nikolova–Karakashian, M. et al., "Bimodal regulation of ceramidase by interleukin–1b" J. Biol. Chem. (1997), vol. 272, No. 30, pp. 18718–18724.
Huwiler, A. et al., "Nitric oxide donors induce stress signaling via ceramide formation is rat renal mesangial cells", J. Biol. Chem. (Mar. 12, 1999), vol. 274, No. 11, pp. 7190–7195.

* cited by examiner

Primary Examiner—Nashaat T. Nashed
(74) Attorney, Agent, or Firm—Birch, Stewart, Kolasch & Birch, LLP

(57) ABSTRACT

A neutral/alkaline ceramidase derived from a mammal; an antibody specifically binding thereto; a probe and primer which are capable of specifically hybridizing thereto; a method for producing the ceramidase by a genetic engineering means; a method for detecting the ceramidase or the gene; and a method of controlling an amount of a ceramide in a cell and/or in a tissue. The present invention is useful as a reagent for lipid engineering for analyzing a structure, functions, and the like of a ceramide, and in its applications to diseases associated with the ceramide metabolism.

14 Claims, 2 Drawing Sheets

CERAMIDASE GENE

This application is the national phase under 35 U.S.C. § 371 of PCT International Application No. PCT/JP00/01802 which has an International filing date of Mar. 24, 2000, which designated the United States of America and was not published in English.

TECHNICAL FIELD

The present invention relates to a polypeptide possessing a ceramidase activity, an antibody specifically binding thereto, a gene encoding the polypeptide, and a probe and primer which are capable of specifically hybridizing thereto, which are useful as a reagent for lipid engineering for analyzing a structure, functions, and the like of a ceramide. In addition, the present invention relates to a method for producing the above-mentioned polypeptide by a genetic engineering means, and a method for detecting the polypeptide or the gene, and a kit therefor. Further, the present invention relates to a method of controlling an amount of a ceramide in a cell and/or in a tissue, which can be applied to a disease caused by abnormality in the amount of the ceramide.

BACKGROUND ART

A ceramidase is an enzyme which hydrolyzes a ceramide, a kind of a sphingolipid, into a sphingoid and a fatty acid. The sphingoid which is generated by hydrolyzing the ceramide with the ceramidase possesses various physiological activities such as inhibition of protein kinase C, activation of phospholipase D and inhibition of a calmodulin-dependent enzyme. As described above, the above-mentioned sphingoid is an important substance which is thought to be acting on the regulation of the cell functions because the sphingoid is involved in proliferation of cells and intracellular signal transduction. The ceramidase is an enzyme which plays an important role of the control of the amount of the above-mentioned sphingoid.

Ceramidases are classified into acidic ceramidases and neutral/alkaline ceramidases by the optimum pH. There have been, so far reported that the presence of a ceramidase possessing the optimum pH in an acidic range has been found in mammalian tissues such as rat brain [$Biochemistry$, 8, 1692–1698 (1969)], guinea pig epithelial cells [$J.\ Biol.\ Chem.$, 270, 12677–12684 (1995)], human kidney [$Biochim.\ Biophys.\ Acta$, 398, 125–131 (1975)], spleen [$Biochim.\ Biophys.\ Acta$, 1004, 245–251 (1989)], fibroblasts [$Biochem.\ J.$, 205, 419–425 (1982)], and epithelium [$FEBS\ Lett.$, 268, 110–112 (1990)]; and human urine [$J.\ Biol.\ Chem.$, 270, 11098–11102 (1995)], and the like.

In addition, it has been clarified that a bacterium belonging to the genus Pseudomonas produces a ceramidase, and this ceramidase is a ceramidase possessing optimum pH in an alkaline region [$J.\ Biol\ Chem.$, 273, 14368–14373 (1998)].

Among these ceramidases, amino acid sequences of the acidic ceramidase purified from human urine and nucleotide sequences of a gene encoding the ceramidase have been determined [$J.\ Biol\ Chem$, 271, 33110–33115 (1996)]. In addition, an acidic ceramidase gene of a mouse has been obtained by utilizing its homology with the above-mentioned acidic ceramidase gene derived from human urine [$Genomics$, 50, 267–274 (1998)].

However, since all of the ceramidase genes derived from mammals which have been reported encode acidic ceramidases, amino acid sequences and genomic structures of the neutral/alkaline ceramidase in mammals have been completely unknown, so that biological functions of the neutral/alkaline ceramidase in higher organisms have not yet been elucidated at present.

In the studies on the elucidation of the in vivo functions of a ceramide, metabolic control therefor, diagnosis or treatment of a disease associated with the ceramide or the like, it is necessary to obtain detailed information concerning various enzymes associated with the ceramide, and the enzyme gene. However, as mentioned above, findings on the amino acid sequence and genes thereof of the neutral/alkaline ceramidase in mammals have not yet been obtained at present. Therefore, in order to develop the technique as described above pertaining to a ceramide, it is necessary to obtain some findings associated with a neutral/alkaline ceramidase, especially a gene thereof.

As mentioned above, although several reports have been made on cloning of ceramidase genes of a mammal, all of these reports are concerned with ceramidases possessing an activity in an acidic region, which cannot be expected to possess a homology with a ceramidase possessing an activity in a neutral/alkaline region. Therefore, it has been difficult to obtain a neutral/alkaline ceramidase gene as a homolog of a nucleotide sequence of the acidic ceramidase gene.

DISCLOSURE OF INVENTION

The present invention has been accomplished in view of the above-described prior art and a first object of the present invention is to provide a neutral/alkaline ceramidase gene of a mammal. A second object of the present invention is to provide a method for producing a neutral/alkaline ceramidase gene in a high purity by a genetic engineering means, comprising using a transformant resulting from incorporation of an expression vector carrying the gene. A third object of the present invention is to provide a polypeptide encoding the above-mentioned gene. A fourth object of the present invention is to provide an antisense DNA and an antisense RNA which are complementary to the gene of the present invention or a part thereof. A fifth object of the present invention is to provide a synthetic oligonucleotide probe or primer capable of specifically hybridizing to the gene of the present invention. A sixth object of the present invention is to provide an antibody or a fragment thereof specifically binding to the polypeptide. A seventh object of the present invention is to provide a method for detecting the above-mentioned ceramidase or a gene thereof, and a kit used therefor. An eighth object of the present invention is to provide a method of controlling an amount of ceramide in the cell or in the tissue.

The present inventors have succeeded in isolating a neutral/alkaline ceramidase from liver of a mouse, a mammalian, and isolating the genes. In addition, they have succeeded in elucidating the structure of the neutral/alkaline ceramidase of a mammal including human by using techniques such as hybridization or polymerase chain reaction (PCR). Further, they have also succeeded in conveniently producing a neutral/alkaline ceramidase in a high purity by genetic engineering techniques by using the genes. Thus, the present invention has been perfected thereby.

Specifically, the gist of the present invention relates to:

[1] a gene having a nucleotide sequence of a nucleic acid selected from the group consisting of:

(A) a nucleic acid encoding a polypeptide having the amino acid sequence of SEQ ID NO: 14 of the Sequence Listing or a partial sequence thereof, the polypeptide possessing a ceramidase activity;

(B) a nucleic acid having a nucleotide sequence of SEQ ID NO: 15 of the Sequence Listing or a partial sequence thereof and encoding a polypeptide possessing a ceramidase activity;

(C) a nucleic acid encoding a polypeptide consisting of an amino acid sequence resulting from deletion, addition, insertion or substitution of at least one amino acid residue in the amino acid sequence of SEQ ID NO: 14 of the Sequence Listing, the polypeptide possessing a ceramidase activity;

(D) a nucleic acid consisting of a nucleotide sequence resulting from deletion, addition, insertion or substitution of at least one base in the nucleotide sequence of SEQ ID NO: 15 of the Sequence Listing and encoding a polypeptide possessing a ceramidase activity;

(E) a nucleic acid capable of hybridizing to a complementary strand of a nucleic acid of any one of the above (A) to (D), under stringent conditions, and encoding a polypeptide possessing a ceramidase activity; and (F) a nucleic acid having a nucleotide sequence different from the nucleic acid of any one of above (A) to (E) via degeneracy and encoding a polypeptide possessing a ceramidase activity;

[2] a recombinant DNA comprising the gene of item [1] above;

[3] an expression vector for a microorganism, an animal cell or a plant cell, comprising the gene of item [1] above or the recombinant DNA of item [2] above;

[4] a transformant carrying the expression vector of item [3] above;

[5] a method for producing a polypeptide possessing a ceramidase activity, characterized by culturing the transformant of item [4] above under conditions appropriate for expression of the ceramidase gene and production of the polypeptide encoded by the gene, and collecting a polypeptide possessing a ceramidase activity from the resulting culture;

[6] a polypeptide having the amino acid sequence of SEQ ID NO: 14 of the Sequence Listing or a partial sequence thereof and possessing a ceramidase activity;

[7] a polypeptide possessing a ceramidase activity, encoded by the gene of item [1] above;

[8] an antisense DNA which is complementary to the gene of item [1] above or a part thereof;

[9] an antisense RNA which is complementary to the gene of item [1] above or a part thereof;

[10] an expression vector comprising the antisense DNA of item [8] above;

[11] an oligonucleotide probe or primer, capable of specifically hybridizing to the gene of item [1] above or a complementary strand thereof;

[12] an antibody or a fragment thereof, capable of specifically binding to the polypeptide of item [6] or item [7] above;

[13] a method for detecting a gene encoding a polypeptide possessing a ceramidase activity, comprising using the oligonucleotide probe or primer of item [11] above;

[14] a kit for the use in detection of a gene encoding a polypeptide possessing a ceramidase activity, comprising the oligonucleotide probe and/or primer of item [11] above;

[15] a method for detecting a polypeptide possessing a ceramidase activity, comprising using the antibody or a fragment thereof of item [12] above;

[16] a kit for the use in detection of a polypeptide possessing a ceramidase activity, comprising the antibody or a fragment thereof of item [12] above; and

[17] a method of controlling an amount of ceramide in a cell and/or in a tissue, characterized by introducing the gene of item [1] above or an antisense nucleic acid thereof into the cell and/or the tissue, thereby controlling the amount of ceramide in the cell and/or in the tissue.

BEST MODE FOR CARRYING OUT THE INVENTION

Figure 1:
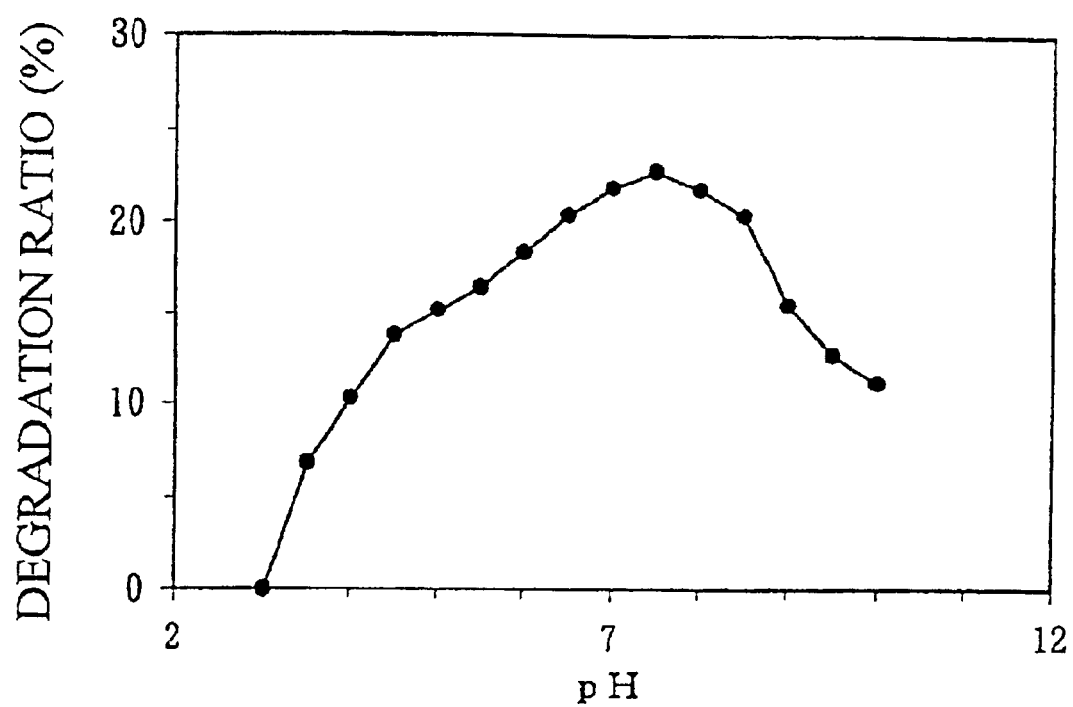
FIG. 1 is a graph showing optimum pH of the ceramidase.

Since information such as consensus sequences for a neutral/alkaline ceramidase has not been clarified, the present inventors have obtained the amino acid information by isolating the above-mentioned neutral/alkaline ceramidase, whereby a gene encoding the above-mentioned ceramidase could be isolated for the first time.

From the above findings, there could be obtained a surprising finding that the amino acid sequence of the neutral/alkaline ceramidase derived from a mouse liver of the present invention has a low homology with the amino acid sequence of a known alkaline ceramidase [previously mentioned, *J. Biol. Chem.*, 273, 14368–14373 (1998)] derived from a bacterium belonging to the genus Pseudomonas (*Pseudomonas aeruginosa*).

The ceramidase of the present invention has been clarified for the first time as a neutral/alkaline ceramidase derived from a mammal. Therefore, the present invention is even more useful in the developments of elucidation of the in vivo functions of a ceramide, metabolic control therefor, and diagnosis and treatment of diseases associated with a ceramide, and the like, as compared to the known alkaline ceramidase derived from the known bacterium of the genus *Pseudomonas*.

The present invention will be described hereinbelow.

(1) Polypeptide Possessing Ceramidase Activity

In the present specification, the phrase "polypeptide possessing a ceramidase activity" (which may be simply referred to as "ceramidase" in the present specification) refers to an enzyme possessing an activity of hydrolyzing a ceramide to generate a sphigoid and a fatty acid as mentioned above. In addition, the term "neutral/alkaline ceramidase" refers to a ceramidase possessing an optimum pH at a pH higher than the acidic range.

As one example thereof, enzymologically chemical and physicochemical characteristics of the isolated and purified, neutral/alkaline ceramidase derived from a mouse liver in the present invention will be described.

1. Action

The ceramidase of the present invention acts to hydrolyze a ceramide, thereby generating a sphingoid and a fatty acid.

The activity of the ceramidase can be determined in accordance with the method described, for instance, in *J. Biol. Chem.*, 275, 3462–3468 (2000).

Concretely, a reaction mixture prepared by dissolving 550 pmol of 12-((N-(7-nitrobenz-2-oxa-1,3-diazol-4-yl)amino) dodecanoyl)sphingosine, hereinafter referred to as C12-NBD-ceramide [*Anal. Biochem.*, 263, 183–188 (1998)], 1.0% (W/V) sodium cholate and a suitable amount of an enzyme (ceramidase) in 20 $\mu$l of 25 mM Tris-hydrochloric acid buffer (pH 7.5) is incubated at 37° C. for 30 minutes. The reaction mixture is incubated in a boiling water bath for 5 minutes, thereby stopping the reaction. The resulting reaction mixture is further evaporated to dryness under reduced pressure. The dried solid is dissolved in chloroform/methanol=2/1 (V/V), and developed by silica gel thin layer chromatography (developing solvent: chloroform/methanol/25% aqueous ammonia=90/20/0.5 (V/V/V)). Thereafter, the 12-(N-7-nitrobenz-2-oxa-1,3-diazol-4-yl)amino) dodecanoyl acid, hereinafter referred to as C12-NBD-fatty acid, generated by the above-mentioned reaction is quantified by using CS-9300 Chromatoscanner (manufactured by Shimadzu Corporation) at an excitation wavelength of 475 nm and a fluorescent wavelength of 525 nm. One unit (U) of this enzyme (ceramidase) is defined as an amount of the enzyme required for releasing 1 micromol of the C12-NBD-fatty acid, per one minute under the above-mentioned conditions, resulting from hydrolysis of the C12-NBD-ceramide.

2. Substrate Specificity

Five milliunits of the ceramidase of the present invention is acted on 100 pmol of various kinds of sphingolipids, in which the fatty acid moiety is labeled with $^{14}$C-radioactive isotope, in 20 ml of 25 mM Tris-hydrochloric acid buffer, pH 7.5, containing 1% sodium cholate at 37° C. for 24 hours. The reaction mixture is developed on silica gel thin layer chromatography. Thereafter, the $^{14}$C-labeled sphingolipids and the $^{14}$C-labeled fatty acids generated by the enzymatic reaction are detected and quantified by Imaging Analyzer BAS 1000 (manufactured by Fuji Photo Film). The degradation ratio is calculated from the obtained values. The substrate specificities of the ceramidase of the present invention are shown in Table 1.

As shown in Table 1, the ceramidase of the present invention shows substrate specificities of: (1) hydrolyzing various N-acylsphingosines; (2) not acting on galactosyylceramide, sulfatide, Galb1-3GalNAcb1-4 (NeuAca2-3)Galb1-4Glcb1-1'Cer (GM1a), or sphingomyelin; (3) acting favorably on a ceramide containing sphingenin (d18:1) than a ceramide containing sphinganine (d18:0); (4) being less likely to act a ceramide containing phytosphingosine (t18:0); and the like.

TABLE 1

| Substrate (Structure) | Degradation Ratio (%) |
| --- | --- |
| N-Lauroylsphingosine (C12:0/d18:1) | 63 |
| N-Palmitoylsphingosine (C16:0/d18:1) | 93 |
| N-Stearoylsphingosine (C18:0/d18:1) | 83 |
| N-Palmitoylsphinganine (C16:0/d18:0) | 59 |
| N-Stearoylsphinganine (C18:0/d18:0) | 40 |
| N-Palmitoylphytosphingosine (C16:0/t18:0) | 5 |
| N-Stearoylphytosphingosine (C18:0/t18:0) | 2 |
| 12-((N-(7-nitrobenz-2-oxa-1,3-diazol-4-yl) amino) dodecanoyl) sphingosine (NBD-N-Dodecanoylsphingosine) (NBD-C12:0/d18:1) | 97 |
| 6-((N-(7-nitrobenz-2-oxa-1,3-diazole-4-yl) amino) hexanoyl) sphingosine (NBD-N-Hexanoylsphingosine) (NBD-C6:0/d18:1) | 2 |
| Galactosylceramide (Galb1-1'Cer) | 0 |
| Sulfatide (HSO3-3Galb1-1'Cer) | 0 |
| GM1a(Galb1-3GalNAcb1-4 (NeuAca2-3)Galb1-4Glcb1-1'Cer) | 0 |
| Sphingomyelin (Choline phosphate Cer) | 0 |

3. Optimum pH

Sixteen milliunits of the ceramidase of the present invention is acted on 100 pmol of C12-NBD-ceramide in 20 ml of 3,3-dimethylglutaric acid, 50 mM Tris-(hydroxymethyl) aminomethane, 50 mM 2-amino-2-methyl-1,3-propanediol at 37° C. for 24 hours. The resulting reaction mixture is developed by silica gel thin layer chromatography. Next, the NBD-labeled ceramide and the NBD-labeled fatty acid generated by the enzymatic reaction are detected and quantified at a detection wavelength of 525 nm by using the CS-9300 Chromatoscanner. The degradation ratio is calculated from the obtained values. FIG. 1 is a graph showing the relationship between the degradation activity of the C12-NBD-labeled ceramide and pH, wherein the ordinate axis shows the degradation ratio (%), and the abscissa axis shows a reaction pH. As shown in the results of FIG. 1, the optimum pH of the present ceramidase is from 7.0 to 8.0.

4. Temperature Stability

The ceramidase of the present invention does not show the reduced activity when treated in 20 mM Tris-hydrochloric acid (pH 7.5) buffer containing 0.1% polidocanol [trade name: Lubrol PX] at 37° C. for 24 hours, but shows the reduced activity by a treatment at 60° C. for 1 hour, to about 30% of the activity before the treatment.

5. Molecular Weight

The molecular weight of the ceramidase of the present invention is about 94 kDa on SDS-PAGE (under reducing conditions). In addition, the present enzyme digested by glycopeptidase F is about 73 kDa on SDS-PAGE (under reducing conditions).

In the present specification, one example of the "polypeptide possessing a ceramidase activity" includes a polypeptide of a naturally occurring ceramidase derived from a mouse, having the amino acid sequence of SEQ ID NO: 14 of the Sequence Listing. Further, not only the polypeptide having the amino acid sequence, but also a polypeptide having an amino acid sequence with a mutation such as substitution, deletion, addition or insertion of one or more amino acids introduced into the amino acid sequence of SEQ ID NO: 14 of the Sequence Listing are encompassed in the term "polypeptide possessing a ceramidase activity," as long as the polypeptide can be found to possess a similar ceramidase activity in accordance with the activity determination by the method described above. In addition, in the above-mentioned mutation, two or more kinds of mutations may be introduced, as long as they are mutations by which the resulting polypeptide can exhibit a ceramidase activity. In the present specification, the term "amino acid sequence with a mutation introduced" encompasses any of amino acid sequences into which a mutation is artificially introduced and amino acid sequences having a naturally occurring mutation.

The ceramidase having the mutation can be concretely obtained, for instance, by selecting a polypeptide possessing a ceramidase activity for the mutated gene having a mutation in the nucleotide sequence (SEQ ID NO: 15) of the ceramidase gene described below, by the following steps:

(a) incubating a gene expression product in a reaction mixture [composition: 550 pmol of C12-NBD-ceramide and 1.0% (W/V) sodium cholate in 20 μl of 25 mM Tris-hydrochloric acid buffer (pH 6 to 9, preferably 6.5 to 8.5, more preferably 7 to 8, especially preferably 7.5)] at 37° C. for 30 minutes, to react the mixture; and (b) detecting generation of a C12-NBD-fatty acid in the reaction product.

(2) Ceramidase Gene

The ceramidase gene in the present invention refers to a gene having a nucleotide sequence of a nucleic acid encoding the above-mentioned "polypeptide possessing a ceramidase activity," or a nucleic acid comprising a nucleotide sequence of the gene. One example thereof includes a gene having a nucleotide sequence of a nucleic acid encoding a polypeptide consisting of the amino acid sequence of SEQ ID NO: 14 of the Sequence Listing or a partial sequence thereof; and a gene having the nucleotide sequence of a nucleic acid consisting of a nucleotide sequence of SEQ ID NO: 15 of the Sequence Listing, or a partial sequence thereof, and the present invention is not limited to these exemplified. As described above, even a gene having a nucleotide sequence of a nucleic acid encoding a polypeptide consisting of a partial sequence of the amino acid sequence of SEQ ID NO: 14, or a gene having a nucleotide sequence of a nucleic acid consisting of a partial sequence of the nucleotide sequence of SEQ ID NO: 15 are encompassed in the scope of the present invention, as long as the gene encodes a polypeptide possessing a ceramidase activity. These genes are neutral/alkaline ceramidase genes derived from mouse liver, and the origin of the ceramidase gene of the present invention is not particularly limited, as long as the ceramidase activity of the gene product can be detected in the same manner as in the steps (a) and (b) described in item (1) above. The origin includes, for instance, mice, rats, humans, hamsters, guinea pigs, and the like.

In the present specification, the phrase "polypeptide consisting of a partial sequence (of the amino acid sequence)" means those in which the ceramidase activity can be detected by the steps (a) and (b) described in item (1) above.

Further, a gene encoding a ceramidase having a mutation, which can exhibit a similar ceramidase activity, is also encompassed in the present invention. For instance, even a gene having a nucleotide sequence of a nucleic acid encoding an amino acid sequence with a mutation such as deletion, addition, insertion or substitution of one or more amino acid residues introduced into the amino acid sequence of SEQ ID NO: 15 of the Sequence Listing is encompassed in the gene of the present invention, as long as the polypeptide encoded by the gene possesses a ceramidase activity. Even a naturally occurring gene having a mutation as well as an artificially prepared gene described above are encompassed in the scope of the present invention, as long as the gene is a gene having a nucleotide sequence of a nucleic acid encoding a polypeptide possessing an activity for a neutral/alkaline ceramidase.

As the method for preparing a gene into which a mutation is artificially introduced as described above, for instance, the following method is used.

As a method of introducing a random mutation, there can be employed, for instance, a method for generating a transition mutation in which cytosine base is substituted by uracil base with a chemical treatment using sodium hydrogen sulfite [*Proceedings of the National Academy of Sciences of the USA*, 79, 1408–1412 (1982)]; a method for lowering an accuracy of incorporation of nucleotide during DNA synthesis by carrying out PCR in a reaction mixture containing manganese [*Anal. Biochem.*, 224, 347–353 (1995)]; and the like.

As a method for introducing site-directed mutagenesis, there can be employed, for instance, a method utilizing amber mutation [gapped duplex method, *Nucleic Acids Research*, 12, 9441–9456 (1984)]; a method of utilizing a dut (dUTPase) gene and ung (uracil-DNA glycosilase) gene deficient host [Kunkel method, *Proceedings of the National Academy of Sciences of the USA*, 82, 488–492 (1985)]; a method by PCR utilizing amber mutation (WO 98/02535); and the like. Various kinds of kits for introducing site-directed mutagenesis to a desired gene by these methods are commercially available, and a gene resulting from introduction of a desired mutation can be readily obtained by utilizing the kits.

In addition, the nucleic acid capable of hybridizing to a complementary strand of the above-mentioned nucleic acid under stringent conditions, the gene having a nucleotide sequence of a nucleic acid encoding a polypeptide possessing a ceramidase activity is also encompassed in the gene of the present invention. The ceramidase activity can be detected, for instance, by the steps (a) and (b) described in item (1) above.

Here, the term "stringent conditions" refers to, for instance, the following conditions. Concretely, the term refers to conditions of carrying out incubation at 50° C. for 4 hours to overnight in 6×SSC (wherein 1×SSC is 0.15 M NaCl, 0.015 M sodium citrate, pH 7.0) containing 0.5% SDS, 5×Denhardt's [0.1% bovine serum albumin (BSA), 0.1% polyvinyl pyrrolidone, 0.1% Ficol 400], and 100 µg/ml salmon sperm DNA.

Also, the details of the hybridization manipulations are described, for instance, in *Molecular Cloning: A Laboratory Manual*, 2nd Ed., published by Cold Spring Harbor Laboratory in 1989, edited by T. Maniatis et al.

The gene having a nucleotide sequence different from the nucleic acid mentioned above via a degenerated genetic code is also encompassed in the ceramidase gene of the present invention.

The polypeptide encoded by the gene of the present invention is encompassed in the present invention, as long as its ceramidase activity can be detected by the steps (a) and (b) described in item (1) above.

According to the gene of the present invention, there is further provided a recombinant DNA suitable for various purposes used. Here, the term "recombinant DNA" refers to a DNA carrying the gene of the present invention, obtained by genetic engineering technique.

The recombinant DNA carrying the ceramidase gene of the present invention is ligated to a known vector or the like, whereby an expression vector inserted with the ceramidase gene in an expressible state can be prepared. Such an expression vector is also encompassed in the present invention.

In the present invention, an expression vector refers to a vector which is constructed such that the gene or recombinant DNA mentioned above is inserted and expressed in desired host cells. In addition, a vector in which an antisense DNA as described below is inserted is also encompassed in the expression vector of the present invention. The vector to be inserted includes plasmid vectors, phage vectors, viral vectors, and the like. As the plasmid vector, commercially available products such as pUC18, pUC19, pBluescript and pET can be suitably used, and as the phage vectors, commercially available products of lambda phage vectors such as λgt10 and λgt11 can be suitably used, without being limited thereto. As the viral vectors, retroviral vector, adenoviral vector, vaccinia viral vector, adeno-associated viral vector, and the like can be used, without being limited thereto. These vectors are appropriately selected in accordance with the host cells used. Each of these vectors may appropriately carry a factor such as an inducible promoter, a selectable marker gene, or a terminator.

In addition, in order to facilitate isolation and purification, a vector carrying a sequence capable of expressing as His tag or GST fusion protein may be used depending upon its use. In this case, GST (glutathione S-transferase) fusion protein vector carrying an appropriate promoter (for instance, lac, tac, trc, trp, CMV, SV40 early promoter, or the like) which functions in a host cell (for instance, pGEX4T), a vector carrying a tag (for instance, Myc, HisA, or the like) sequence or the like can be used.

(3) Transformant Harboring Ceramidase Gene

The transformant of the present invention, namely the cells capable of expressing the ceramidase gene of the present invention, can be obtained by transforming a host with an expression vector in which the ceramidase gene of the present invention is inserted. The host-used can be appropriately selected depending upon the purposes used of the desired ceramidase, and microorganisms such as *Escherichia coli*, yeasts, animal cells, plant cells, animal individuals, plant individuals, and the like. Concretely, *Escherichia coli* includes HB101 strain, C600 strain, JM109 strain, DH5α strain, DH10B strain, XL-1BlueMRF' strain, TOP10F strain and the like of the *Escherichia coli* K-12 derivative. Also, the yeast cells include *Saccharomyces cerevisiae* and the like. The animal cells include L, 3T3, FM3A, CHO, COS, Vero, Hela, and the like. The plant cells include tobacco BY2 and the like.

As a method for transducing an expression vector into a host, a method, including, for instance, described in *Molecular Cloning: A Laboratory Manual*, 2nd Ed., 249–254 may be employed. Next, in order to select a transformant expressing a desired gene, the characteristics of the expression vector are utilized. For instance, in a case where a plasmid vector is pBluescript and a host cell *Escherichia coli*, a colony having ampicillin resistance on a plate containing ampicillin is selected, or a colony having ampicillin resistance and showing white color on a plate containing ampicillin, 5-bromo-4-chloro-3-indolyl-β-D-galactoside (X-Gal) and isopropyl-β-D-thiogalactopyranoside (IPTG) is selected, thereby selecting a colony in which a foreign gene is transduced.

The polypeptide possessing a ceramidase activity can be produced by culturing the transformant of the present invention under generally employed conditions. In some cases, the codon usage differs depending upon a host in which the gene of the present invention is expressed, so that expression is suppressed. In this case, the codon used in the gene of the present invention may be changed to a codon suitable to each host. In addition, the above-mentioned expression vector is not limited only to those vectors derived from plasmids, and vectors derived from phages, cosmids, and the like may also be used, as long as the object of the present invention is not hindered. A vector capable of inducing and expressing a foreign gene, a vector capable of expressing as a fusion protein with a reporter gene product, and the like are desirable, from the viewpoint of readily and massively producing the polypeptide of the present invention.

The expression of the ceramidase can be confirmed by determining the ceramidase activity. The activity can be determined by, for instance, the method described in *J. Biol. Chem.*, 275, 3462–3468 (2000) using a cell extract of the transformant as a sample, for instance, similar procedures to the steps (a) and (b) described in item (1) above. In addition, the expression of the ceramidase can be confirmed by determining the amount of a ceramide in the cell. The above-mentioned amount of ceramide can be determined, for instance, by the method described in *Analytical Biochemistry*, 244, 291–300 (1997). Also, an antibody against the ceramidase can be used. In a case where the ceramidase is expressed as a fusion body with another polypeptide (the polypeptide excluding the ceramidase of the present invention), an antibody against this polypeptide moiety, the polypeptide excluding the ceramidase of the present invention, may be used. In a case where an antibody is used, the ceramidase can be detected by, for instance, subjecting a cell extract of the transformant to electrophoresis on an SDS-polyacrylamide gel, and thereafter transferring the electrophoresed gel on a polyvinylidene fluoride (PVDF) membrane, and detecting with the antibody on this membrane.

(4) Method for Producing Polypeptide Possessing Ceramidase Activity

The present invention also provides a method for producing a polypeptide possessing a ceramidase activity, comprising the steps of culturing the above-mentioned transformant under conditions appropriate for expression of the ceramidase gene of the present invention and production of the polypeptide encoding the gene, and collecting a polypeptide possessing a ceramidase activity from the resulting culture. The method for culturing the transformant is not particularly limited, and an appropriate one can be selected from a known culturing method appropriate for the host used.

In the production method of the present invention, in a case where the above-mentioned transformant is a microorganism or a cultured cell, the ceramidase can be efficiently produced by determining optimum conditions for expression of the ceramidase in a medium composition, a pH of a medium, a culturing temperature, and a culturing time, as well as the amount of an inducer used, and the using time period, and the like.

A general method is employed in the purification of the ceramidase from the culture of the transformant. In a case where the transformant intracellularly accumulates the ceramidase as in the case of *Escherichia coli*, after the termination of culture, the transformant cells are harvested by centrifugation, and the resulting cells are disrupted by sonication or the like, and thereafter centrifuged or the like to give a cell-free extract. The cell-free extract used as a starting material can be purified by salting-out as well as a general protein purification method such as various kinds of chromatographies such as ion-exchange chromatography, gel filtration chromatography, hydrophobic chromatography, and affinity chromatography. The expression product may be extracellularly secreted depending upon the host-vector system used in some cases. In such a case, the purification can be similarly carried out from culture supernatant.

According to the method of the present invention, in a case where the ceramidase is produced intracellularly, a desired ceramidase may coexist intracellularly with impurities such as various kinds of enzymes and proteins. Since the impurities are present in a trace amount as compared to the amount of the expressed ceramidase, there is an excellent advantage that its purification is extremely facilitated. In addition, in a case where an extracellular secretion-type vector is used as a vector, the ceramidase is extracellularly secreted, so that the medium component or the like coexists in the fraction comprising the ceramidase. However, since the fraction usually contains almost no protein component which would hinder the ceramidase purification, there is an excellent advantage in that, for instance, complicated separation and purification procedures which have been required in the purification of the ceramidase from a mouse liver are not necessitated In addition, in a case of a ceramidase derived from a fungus, there is a possibility that the enzyme itself has a sugar chain. A polypeptide possessing a ceramidase activity and having no sugar chain can be produced by using as a host cell a cell which does not possess a sugar chain-synthesizing ability, for instance, a mutant cell which has lost a sugar chain-synthesizing ability of a prokaryote such as *Escherichia coli, Bacillus substilis* or Actinomyces, or an yeast, a fungus, an animal cell, an insect cell and a plant cell. Further, an enzyme having a sugar chain can be produced. In this case, a polypeptide possessing a ceramidase activity and having a sugar chain can be produced by using as a host cell a cell which possesses a sugar chain-synthesizing ability, for instance, an yeast, a fungus, an animal cell, an insect cell and a plant cell.

Also, the expression product may form an insoluble inclusion body depending upon the host-vector system used. In this case, after the termination of culture, the transformant cells are harvested by centrifugation, and the resulting cells are disrupted by sonication or the like, and thereafter centrifuged or the like, thereby harvesting an insoluble fraction containing the inclusion body. After washing the inclusion body, the inclusion body is solubilized with an generally used protein solubilizing agent, for instance, urea, guanidine hydrochloride, or the like, and purified by various kinds of chromatographies such as ion-exchange chromatography, gel filtration chromatography, hydrophobic chromatography, and affinity chromatography as occasion demands. Thereafter, refolding procedures employing dialysis or dilution method are carried out, whereby a preparation comprising a polypeptide possessing a ceramidase activity can be obtained. If this preparation is further purified by various kinds of chromatographies as occasion demands, a polypeptide possessing a ceramidase activity in a high purity can be obtained.

(5) Probe for Hybridization and Primer for PCR

The oligonucleotide probe or primer of the present invention is capable of specifically hybridizing to the gene of the present invention, or a complementary strand thereof. The oligonucleotide probe or primer is designed on the basis of the nucleotide sequence of the ceramidase gene of the present invention. For instance, the oligonucleotide probe or primer can be prepared by chemical synthesis by a general method. The nucleotide sequence for the oligonucleotide probe is not particularly limited. The nucleotide sequence is those capable of hybridizing to the above-mentioned ceramidase gene, or a nucleic acid having a nucleotide sequence complementary to the gene under stringent conditions. The above-mentioned term "stringent conditions" is not particularly limited. For instance, the term "stringent conditions" refers to conditions of incubating overnight at a temperature of [(Tm of the above-mentioned probe)—25° C.] in a solution containing 6×SSC, 0.5% SDS, 5×Denhardt's, and 100 mg/ml salmon sperm DNA, and the like. Also, the nucleotide sequence of the above-mentioned primer is not particularly limited, as long as the primer is annealed to the above-mentioned ceramidase gene or the gene having a nucleotide sequence complementary to the gene under usual reaction conditions for PCR so that the extension reaction by the DNA polymerase can be initiated.

Tm of the oligonucleotide probe or primer can be calculated, for instance, by the following equation:

$$Tm=81.5-16.6(\log_{10}[Na^+])+0.41(\% \ G+C)-(600/N)$$

wherein N is a chain length of the oligonucleotide probe or primer; and % G+C is a content of guanine and cytosine residues in the oligonucleotide probe or primer.

In addition, when the chain length of the oligonucleotide probe or primer is shorter than 18 bases, Tm can be deduced from a product of the contents of A+T (adenine+thymine) residues multiplied by 2° C., with a sum of a product of the contents of G+C residues multiplied by 4° C. [(A+T)×2+ (G+C)×4].

The chain length of the above-mentioned oligonucleotide probe is not particularly limited. It is preferable that the chain length is 15 bases or more, more preferably 18 bases or more, from the viewpoint of preventing nonspecific hybridization.

In addition, as the primer of the present invention, there can be cited the nucleic acids having the same nucleotide sequences as those for the above-mentioned oligonucleotide probe. For instance, the primer can be prepared by, for instance, designing on the basis of the nucleotide sequence of the gene of the present invention, and chemically synthesizing it, and the like. The chain length of the primer is not particularly limited. For instance, the primer having a chain length of 15 to 40 bases can be used, especially one having a chain length of 17 to 30 bases can be suitably used. The above-mentioned primer can be used for various gene amplification methods such as PCR method, whereby the ceramidase gene of the present invention can be detected.

Also, as the above-mentioned oligonucleotide probe or primer, there may be used a nucleic acid obtained by fragmenting a nucleic acid encoding a naturally occurring ceramidase by an enzymatic treatment such as endonuclease treatment or exonuclease treatment, a physical treatment such as sonication, or the like, and subjecting the resulting fragment to separation and purification by various kinds of nucleic acid separation methods represented by agarose gel or the like. It is desired that the nucleic acid obtained as described above is derived from a region having a sequence characteristic of the ceramidase.

Further, in order to more readily detect the nucleic acid to be detected, the above-mentioned oligonucleotide probe or primer can be subjected to appropriate labeling in accordance with a known method to be used in the detection of the ceramidase gene of the present invention. The labeling is not particularly limited. The oligonucleotide probe or primer may be labeled with radioisotopes as well as various labels represented by fluorescent substances, and ligands such as biotin and digoxigenin.

A DNA having high homology to the ceramidase gene of the present invention can be cloned by screening a genomic DNA or cDNA derived from an organ other than a mouse liver or from an organism other than a mouse, or a genomic DNA library or cDNA library, by using the probe for hybridization of the present invention.

In addition, a DNA fragment having high homology to the ceramidase gene of the present invention can be detected by PCR method from a genomic DNA or cDNA derived from an organ other than mouse liver or derived from an organism other than mouse, or a genomic DNA library or cDNA library, by using the primer of the present invention, and further its full length gene can also be obtained.

(6) Method for Detecting Gene

One of the big features of the method for detecting a gene of the present invention resides in that the gene in the sample to be detected is detected by using the above-mentioned oligonucleotide probe and/or primer.

In the method for detection of the present invention, the gene may be detected by hybridization method or the like by using the above-mentioned oligonucleotide probe, or the gene may be detected by DNA amplification method such as PCR method by using the above-mentioned primer.

In a case of hybridization using the oligonucleotide probe, the samples to be detected include, for instance, samples such as colonies and cultured cells of microorganisms, and tissue fragments, those obtained by immobilizing DNA or RNA in these samples onto a membrane, DNA or RNA extracted from these samples, and the like.

The hybridization can be carried out in accordance with a known method described in *Molecular Cloning: A Laboratory Manual*, 2nd Ed. and the like. The conditions for the hybridization can be appropriately determined by the Tm value of the probe used, the GC content of the target DNA, and the like. For instance, the conditions described in *Molecular Cloning: A Laboratory Manual*, 2nd Ed. mentioned above or the like can be applied.

In a case where the gene is detected by using the primer, the samples to be detected include, for instance, microorganism samples such as culture of microorganisms, colonies of microorganisms and bacterial cells of microorganisms; samples derived from a living body such as cultured cells, tissues and tissue fragments; and the like. As these samples, for instance, isolated microorganisms and cultured cells may be used in the original states, or after being subjected to an appropriate treatment. In addition, solid samples such as tissues can be used by preparing an exudate or suspension. Also, supernatant of these samples, or those samples prepared by subjecting these samples to a cytolytic treatment such as a treatment with a surfactant or supernatant thereof can be used. Further, the sample may be subjected to a procedure of removing other components in the sample within a range so as not to impair the nucleic acid to be detected.

In a case where the detection is carried out by PCR method by using the above-mentioned primer, the PCR conditions can be appropriately selected in accordance with the Tm value of the primer used, the length of the region to be amplified and detected, and the like. In PCR, the desired gene can be detected by confirming the presence or absence of the amplified product. The method for confirming the presence or absence of amplification is not particularly limited. For instance, the confirmation can be made by, for instance, subjecting a reaction mixture for nucleic acid amplification to agarose gel electrophoresis, staining the gel with an appropriate nucleic acid staining reagent, such as ethidium bromide or SYBER Green I, subjecting the gel to irradiation with ultraviolet rays, and detecting the presence or absence of the band. The detection of the band may be observed by naked eyes, or the detection can be made, for instance, by using a fluorescent image analyzer or the like.

In the method for detecting the gene of the present invention, in order to increase the detection sensitivity, the above-mentioned probe and primer may be used together. For instance, the gene can be detected in high sensitivity and accurately by amplifying the ceramidase gene existing in a trace amount in the sample by PCR method with the above-mentioned primer, and thereafter hybridizing the gene with the probe.

In a case where the ceramidase gene is detected by the method for detection of the present invention and the amount of the gene is further determined, the amount of the gene can be determined by quantifying an intensity of the signal ascribed to the hybridized probe, a fluorescent intensity of the band ascribed to a product amplified with the primer, or the like. The expression amount of the desired gene can be examined by quantifying the amount by using mRNA as an object to be determined.

In addition, in the method for detection of the present invention, the detection can be carried out more conveniently by using the kit for the use in detection of the gene of the present invention. Such a kit is also encompassed in the present invention. One of the features of the above-mentioned kit resides in that the kit comprises the above-mentioned oligonucleotide probe and/or the above-mentioned primer. The above-mentioned kit may contain various components used in the detection procedures. For instance, in a case of a kit comprising an oligonucleotide probe, there may be contained various kinds of reagents for hybridization representatively exemplified by a membrane for immobilizing a nucleic acid, a hybridization buffer, and the like. Also, in a case of a kit comprising a primer, there may be contained reagents for PCR representatively exemplified by thermostable DNA polymerases, dNTP mixed solutions, buffers for PCR, and the like. Further, there may be contained reagents for detecting a probe or an amplified DNA, media for proliferating microorganisms, media for culturing cells, reagents for extracting nucleic acids from a sample, and the like.

(7) Antibody or Fragment Thereof Specifically Binding to Polypeptide Possessing Ceramidase Activity The antibody or a fragment thereof specifically binding to the polypeptide of the present invention is not particularly limited, as long as the antibody or a fragment thereof possesses an ability of specifically binding to the polypeptide. The antibody may be any of polyclonal antibodies and monoclonal antibodies. Further, antibodies modified by known techniques or antibody derivatives, for instance, humanized antibodies, Fab fragments, single-chain antibodies, and the like, can also be used The antibody of the present invention can be readily prepared by appropriately immunizing a rabbit, a rat or a mouse using all or a part of the polypeptide of the present invention in accordance with the method described in, for instance, *Current Protocols in Immunology*, edited by John E. Coligan, published by John Wiely & Sons, Inc., 1992. The antibody thus obtained is purified and thereafter treated with a peptidase or the like, to give an antibody fragment. In addition, the antibody can be prepared by genetically engineering means. Further, the antibody or a fragment thereof of the present invention may be subjected to various modifications in order to facilitate the detection by enzyme immunoassay, fluoroimmunoassay, luminescent immunoassay, or the like.

The antibody or a fragment thereof mentioned above encompasses those which are capable of specifically binding to a certain partial fragment of the polypeptide.

The use of the resulting antibody or a fragment thereof includes applications to detection of ceramidase-producing bacteria, detection of ceramidase-expressed cell lines, detection of ceramidase proteins in the cultured cell or in the tissue, affinity chromatography, screening of an expression product of various kinds of libraries (genomic DNA or cDNA), pharmaceuticals, diagnostic agents, reagents for researches, and the like.

(8) Method for Detecting Polypeptide

A feature of the method for detecting the polypeptide of the present invention resides in that the polypeptide possessing a ceramidase activity is detected by the antibody or a fragment thereof mentioned above.

In the present invention, as the samples to be detected, there can be used, for instance, cultures of microorganisms and animal cells, tissue fragments, cell disruptions of microorganisms and animal cells, extracts or washings of tissues such as skins, and protein samples such as membranes immobilized with proteins derived from microorganisms, animal cells and tissues.

As to the detection of the specific binding of the antibody or a fragment thereof to the above-mentioned polypeptide, a known method can be utilized, and such a method includes, for instance, enzyme immunoassay, fluoroimmunoassay, luminescent immunoassay, and the like.

In the method for detecting the polypeptide of the present invention, the detection can be more conveniently carried out by using the kit for the use in the detection of the polypeptide of the present invention. Such a kit is also encompassed in the present invention. A feature of the above-mentioned kit resides in that the kit comprises the above-mentioned antibody or a fragment thereof. In addition, the kit may contain a reaction buffer, a labeled secondary antibody, a developing reagent, and the like.

(9) Antisense DNA and Antisense RNA

In the present invention, each of the terms "antisense DNA" and "antisense RNA" refers to those having a nucleotide sequence complementary to the ceramidase gene of the present invention or a part thereof, which suppresses or controls expression (transcription, translation) of the genetic information from the gene by forming a double strand with an endogenous ceramidase gene (genomic DNA and mRNA). The length of the antisense DNA or antisense RNA can be changed depending upon the specificity of the nucleotide sequence and the method for transducing the nucleotide sequence into a cell. The antisense DNA or antisense RNA can be prepared by artificially synthesizing with a synthesizer; expressing a gene in an opposite direction (direction of antisense) of the usual direction by an enzymatic reaction with the gene of the present invention as a template; or the like. In a case where expression of the antisense RNA is desired in a living body, an expression vector ligated to the gene of the present invention in an opposite direction of the usual direction is constructed, and the resulting expression vector may be transduced into a living body.

For instance, numerous antisense techniques such as suppression of proliferation of HIV utilizing tat gene [*Nucleic Acids Research*, 19, 3359–3368 (1991)] or rev gene [*Proceedings of the National Academy of Sciences of the USA*, 86, 4244–4248 (1989)] have been known. Therefore, according to these methods, expression of the endogenous ceranudase gene can be suppressed or controlled by using the antisense DNA or antisense RNA of the present invention. In addition, the antisense DNA or antisense RNA of the present invention can be utilized as a research reagent for in situ hybridization or the like.

(10) Control of Amount of Ceramide in Cell or in Tissue Using Ceramidase Gene or Antisense Nucleic Acid Thereof By the gene of the present invention, a method of controlling an amount of a ceramide in a cell and/or in a tissue can be further provided. Such a method of control is also encompassed in the present invention. One of the features of the method of controlling an amount of a ceramide in a cell and/or in a tissue of the present invention resides in that the ceramidase gene of the present invention is introduced into the cell and/or into the tissue, thereby controlling the amount of a ceramide in the cell and for in the tissue.

Concretely, in the method of control of the present invention, the ceramidase gene of the present invention is introduced into the cell and/or into the tissue, and the ceramide is degraded in a cell or in a tissue by an action of the ceramidase expressed by the gene. On the other hand, the ceramidase gene of the present invention is introduced into the cell or into the tissue so as to generate the antisense nucleic acid of the gene, for instance, an antisense RNA, whereby the ceramidase activity in the cell or in the tissue is lowered, so that the degradation of the ceramide can be suppressed. In addition, in a case where the amount of the ceramide is suppressed, the antisense nucleic acid of the ceramidase gene of the present invention, namely the antisense DNA or antisense RNA of the present invention, may be introduced in a cell or in a tissue in an intact form.

As the method for introducing the ceramidase gene or an antisense nucleic acid thereof mentioned above in a cell or in a tissue, a known method can be used, and methods for physically introducing a gene such as electroporation method and particle gun method, or a method for introducing a gene using a viral vector can be utilized. The viral vector which can be used in the method of the present invention is not particularly limited. For instance, the gene can be introduced by using retroviral vector, adenoviral vector, vaccinia viral vector, adeno-associated viral vector, or the like.

According to the method of control of the present invention, the ceramidase gene or an antisense nucleic acid thereof of the present invention is introduced in a cell or in a tissue to control the amount of a ceramide in the cell and/or in the tissue, whereby exhibiting excellent effects such that a disease caused by an abnormal amount of a ceramide can be treated, and that a model animal suffering from a disease with abnormal ceramide metabolism can be prepared. The "disease caused by an abnormal amount of a ceramide" is not particularly limited, and includes, for instance, Farber's disease and the like.

The method for obtaining a ceramidase gene derived from a mouse liver will be explained hereinbelow.

1) First, a membrane fraction is prepared from a homogenate of a mouse liver, and suspended in a sucrose-EDTA solution, and the suspension is frozen and thawed, and thereafter centrifuged, to give supernatant (crude enzyme extract). A ceramidase preparation homogeneously purified can be obtained from the resulting crude enzyme extract by combining known protein purification methods, for instance, various kinds of chromatographies. As the chromatographies which can be used in the above-mentioned purification, anion exchange chromatography, hydrophobic chromatography, chelating chromatography, gel filtration chromatography, and the like can be used.

2) Next, as the information for preparing a probe for cloning the ceramidase gene, the partial amino acid sequences of the ceramidase are examined. The N-terminal amino acid sequence of the ceramidase can be found by subjecting the above-mentioned purification ceramidase preparation itself to amino acid sequencing by Edman degradation method [*J. Biol. Chem.*, 256, 7990–7997 (1981)]. In addition, the partial amino acid sequence of the internal ceramidase can be obtained by purifying an appropriate peptide fragment from a peptide mixture resulting from digestion of the purified enzyme preparation with a protease having a high substrate specificity, for instance, lysylendopeptidase, N-tosyl-L-phenylalanyl chloromethyl ketone (TPCK)-trypsin, and the like, and subjecting the resulting fragment to amino acid sequencing.

3) On the basis of the information of the amino acid sequence thus clarified, an oligonucleotide to be used for the probe for hybridization, or used for the primer for PCR is designed, to clone the ceramidase gene of the present invention. In order to carry the cloning, PCR or hybridization method generally employed is utilized. PCR method can be carried out in accordance with the method described in PCR Technology, edited by Erlich, H. A., published by Stockton Press, 1989. The hybridization method can be carried out, for instance, in accordance with a known method described in *Molecular Cloning: A Laboratory Manual*, 2nd Ed.

4) As to the DNA fragment obtained by the hybridization or PCR mentioned above, by decoding its nucleotide sequence, the amino acid sequence which can be encoded therein can be known. Whether or not the above-mentioned DNA fragment is a fragment of the ceramidase gene can be confirmed by comparing the sequence with the partial amino acid sequence of the ceramidase obtained in item 2) above.

5) In a case where the DNA fragment obtained by hybridization or PCR in item 3) is a part of the ceramidase gene, a DNA fragment comprising a gene encoding a full length ceramidase can be obtained by repeating the procedures of item 3), or alternatively, preparing a new probe or primer on the basis of the nucleotide sequence of the DNA fragment obtained in item 3), and carrying out hybridization or PCR by using the probe or primer.

6) An expression vector is constructed by ligating the gene encoding a full length ceramidase thus obtained with an appropriate vector, and then the transformant in which the expression vector is transduced is prepared. The transformant is cultured, and the ceramidase activity in the resulting culture is examined, whereby confirmation can be made such that the resulting gene is one encoding the ceramidase.

However, in the cloning of the ceramidase gene of the present invention, a probe DNA appropriate for screening of the library by hybridization method could not be designed on the basis of the partial amino acid sequence information obtained in the present invention. In addition, although various PCR primers were designed by designing from each of the partial amino acid sequences and the nucleotide sequences of vector for the use in the library preparation, and the resulting primers were used in various combination to carry out PCR, specific amplification was not found, the only amplification being found alone in the combination of two kinds of primers designed on the basis of the partial amino acid sequence C-53 (shown in the amino acid sequence of C-53 in SEQ ID NO: 3 of Sequence Listing). However, the amplified DNA fragment P-1 (shown in the nucleotide sequence of P-1 in SEQ ID NO: 6 of Sequence Listing) was as short as 68 bp, so that the amplified fragment itself could not be used as a probe for library screening by hybridization method. Therefore, a gene fragment of a size of 335 bp, which is thought to be appropriate for the first time as a probe for library screening by hybridization method, has been successfully obtained for the first time by further designing a primer for PCR on the basis of the sequence of P-1, and at the same time carrying out PCR in combination of the primer and a primer designed on the basis of the nucleotide sequence of a vector used in the preparation of the library.

Further, a gene encoding a full length ceramidase can be cloned by screening cDNA library derived from a mouse liver with the above-mentioned fragment of a size of 335 bp as a probe. Also, the genomic DNA of a ceramidase of the present invention can be obtained by screening a genomic DNA library derived from a mouse liver.

The entire nucleotide sequence of the produced ceramidase gene from a mouse liver thus obtained is shown in SEQ ID NO: 12 of Sequence Listing, and the amino acid sequence of the polypeptide encoded thereby is shown in SEQ ID NO: 13 of Sequence Listing. It has been found that the enzyme is processed to a mature enzyme in which the N-terminal part of the peptide of the gene is removed in vivo on the bases of this amino acid sequence and the N-terminal amino acid sequence of the gene. The amino acid sequence of this mature ceramidase and the nucleotide sequence encoded by the sequence are shown in SEQ ID NOs: 14 and 15 of Sequence Listing, respectively. Each of the above-mentioned amino acid sequence and nucleotide sequence does not have homology with each of the known amino acid sequence and nucleotide sequence of a ceramidase derived from a mammal. In other words, the ceramidase gene provided by the present invention consists of a completely novel sequence, which is irrelevant to the known ceramidase gene.

As described above, according to the present invention, there are provided a primary structure and a genetic structure of the ceramidase derived from a mouse liver. Further, there can be carried out a method for producing a polypeptide possessing a ceramidase activity inexpensively and in a high purity by genetic engineering means.

In addition, the oligonucleotide probe or primer capable of specifically hybridizing to the ceramidase gene of the present invention is useful in searching, detection, amplification and the like of the ceramidase gene of the present invention. The antibody or a fragment thereof specifically binding to the polypeptide of the present invention is useful in detection, identification, purification, and the like of a ceramidase.

In addition, according to the method of controlling an amount of a ceramide in a cell and/or in a tissue of the present invention, the amount of a ceramide in the cell and/or in the tissue can be controlled by introducing the ceramidase gene of the present invention or its antisense nucleic acid into the cell and/or into the tissue. Therefore, such a method of control is useful in the treatment of a disease caused by an abnormal ceramide amount, for instance, but not being particularly limited thereto, a treatment of a disease such as Farber's disease.

The present invention will be concretely explained by the examples, without by no means intending to limit the scope of the present invention to these examples.

EXAMPLE 1

Purification of Ceramidase

In 300 ml of a 0.25 M sucrose solution containing 1 mM EDTA (sucrose-EDTA solution) was homogenized 181 g of livers excised from 105 Sea/ddY mice (produced by Seiwa Experimental Animals). The resulting homogenate was centrifuged at 600×g for 10 minutes, and thereafter the supernatant was collected. The resulting supernatant was further centrifuged at 2700×g for 30 minutes, and the precipitates were collected.

The precipitated fraction was suspended in 480 ml of the sucrose-EDTA solution to give a suspension. The resulting suspension was frozen at −80° C., and thereafter thawed under running water. This freezing-thawing treatment was repeated twice. Thereafter, the treated suspension was centrifuged at 105000×g for 90 minutes, and supernatant and precipitates were each collected. The precipitates were subjected to the treatments of freezing-thawing and centrifugation in the same manner as described above. The supernatant was collected, and combined with the previously obtained supernatant, to give 520 ml of a crude enzyme extract.

Two-hundred and sixty milliliters of the crude extract was applied onto 100-ml DEAE-Sepharose FF (manufactured by Amersham Pharmacia) column equilibrated with 20 mM phosphate buffer (pH 7.0) and then non-adsorbent substances were removed by wash. Thereafter, the elution was carried out with the same buffer containing 1 M NaCl to collect 160 ml of an active fraction for ceramidase. The fraction was subsequently applied onto 100-ml Phenyl-Sepharose FF (manufactured by Amersham Pharmacia) column equilibrated with 20 mM Tris-hydrochloric acid buffer (pH 7.5) containing 1 M NaCl. Thereafter, the elution was carried out on a concentration gradient of 2 to 0 M NaCl, and the elution was ether carried out on a concentration gradient of 0 to 1% Polidocanol (trade name: Lubrol PX, manufactured by Nacalai Tesque Inc.). By this chromatography, 310 ml of an active fraction for ceramidase was collected.

The resulting active fraction was applied onto 25-ml Chelating-Sepharose FF (manufactured by Amersham Pharmacia, $Cu^{2+}$ bound type) column equilibrated with 20 mM Tris-hydrochloric acid buffer (pH 7.5) containing 0.5 M NaCl and 0.1% Lubrol PX. The column was washed with the same buffer and then with 20 mM Tris-hydrochloric acid buffer (pH 7.5) containing 0.1% Lubrol PX. Thereafter, the elution of the enzyme was carried out with 20 mM Tris-hydrochloric acid buffer (pH 7.5) containing 2 M NH$_4$Cl and 0.1% Lubrol PX. The eluted active fraction was concentrated by ultrafiltration, to give a concentrate. Next, the buffer in the concentrate was substituted with 20 mM Tris-hydrochloric acid buffer (pH 7.5) containing 0.1% Lubrol PX, to give an enzyme solution. Thirty milliliters of the resulting enzyme solution was further applied onto a porous HQ column (φ4.6×100 mm, manufactured by Perceptive Biosystems) equilibrated with 20 mM Tris-hydrochloric acid buffer (pH 7.5) containing 0.1% Lubrol PX. Subsequently, the elution was carried out on a concentration gradient of 0 to 0.5 M NaCl, to give an active fraction. This active fraction was applied onto hydroxyapatite column (φ7.5×100 mm, manufactured by PENTAX equilibrated with 1 mM phosphate buffer (pH 7.0) containing 0.2 M NaCl and 0.1% Lubrol PX. The ceramidase did not adsorb to this column, and was collected on an effluent column. Thereafter, the fraction was subjected to gel filtration chromatography by using Superose 200HR column (φ10×300 mm, manufactured by Amersham Pharmacia) equilibrated with 20 mM Tris-hydrochloric acid buffer (pH 7.5) containing 0.2 M NaCl and 0.3% Lubrol PX to give a purified ceramidase. As a result of the above purification procedures, 58 mg of a purified ceramidase preparation was obtained.

Various characteristics of the resulting purified ceramidase preparation were studied as described in the present specification. They were found to be as follows:

action: hydrolyzing ceramide to generate a sphingoid and fatty acid;

substrate specificity: having a substrate specificity as shown in Table 1 listed above;

optimum pH: as shown in FIG. 1, the optimum pH of this ceramidase being from 7.0 to 8.0;

temperature stability: the reduced activity not being observed when treated in 20 mM Tris-hydrochloric acid buffer (pH 7.5) containing 0.1% Polidocanol (trade name: Lubrol PX) at 37° C. for 24 hours, but the activity being reduced to about 30% of that before the treatment when treated for 60° C. for 1 hour; and molecular weight: about 94 kDa on SDS-PAGE (under reducing conditions); and about 73 kDa on SDS-PAGE (under reducing conditions) in this enzyme digested by glycopeptidase F.

EXAMPLE 2

Partial Amino Acid Sequencing of Ceramidase

To 11 ml of a sample solution comprising 50 pmol ceramidase was added 20 mM Tris-hydrochloric acid buffer (pH 7.5) containing 0.3% Lubrol PX. The resulting sample solution was applied onto MonoQ PCl 6/5 column (100 μl, manufactured by Amersham Pharmacia). Subsequently, the ceramidase fraction adsorbed to the column was eluted with the same buffer containing 0.4 M NaCl. By these procedures, the ceramidase-containing fraction was concentrated to a volume of 50 μl. The resulting concentrate was subjected to SDS-polyacrylamide gel electrophoresis, and the electrophoresed gel was stained with GelCode Blue Stain reagent (manufactured by Pierce). Next, the band corresponding to the ceramidase was cut out. One-quarter of the cut-out gel fragment was subjected to extraction on 300 μl of 0.1 M Tris-hydrochloric acid buffer (pH 9.0) containing 0.1% SDS at 37° C. for 16 hours. Using the resulting extract as a sample, the N-terminal amino acid sequencing of the ceramidase was performed by using G1005A Protein Sequencing System (manufactured by Hewlett-Packard) to determine an amino acid sequence N-term. SEQ ID NO: 1 of Sequence Listing shows an amino acid sequence N-term.

In addition, the remaining three-quarter of the cut-out gel fragment was washed with 1 ml of 0.5 M Tris-hydrochloric acid buffer (pH 9.2)/50% acetonitrile at 30° C. for 45 minutes. The gel was completely dried by using nitrogen gas and centrifugal concentrator, and thereafter 10 μl of 0.5 M Tris-hydrochloric acid buffer (pH 9.2) containing 0.5 μg of Protease Lys-C (manufactured by Wako Pure Chemical Industries, Ltd.) was added thereto. Further, 0.1 M Tris-hydrochloric acid buffer (pH 9.2) was added until the gel was completely swollen, and the mixture was kept at 37° C. for 16 hours to carry out the protease digestion of the ceramidase. After the termination of the reaction, the procedures of extracting with 150 μl of 0.1% trifluoroacetic acid/60% acetonitrile at room temperature for 1 hour were repeated twice, and an extract was collected. This extract was subjected to reversed phase chromatography to purify the peptide fragment. The resulting peptide fragment was analyzed by Edman degradation method using the G1005A Protein Sequencing System to determine partial amino acid sequences C-46 and C-53. SEQ ID NOs: 2 and 3 of Sequence Listing each shows an amino acid sequence for C-46 and C-53.

EXAMPLE 3

Amplification of DNA Fragment Comprising Ceramidase Gene by PCR Method

Sense mix primer 53-S1 and antisense mix primer 53-A3 were designed and synthesized with a DNA synthesizer on the basis of the partial amino acid sequence C53 of the ceramidase determined in Example 2. SEQ ID NOs: 4 and 5 of Sequence Listing each show the nucleotide sequences of the primers 53-S1 and 53-A3. PCR was carried out by using these primers. PCR was carried out with mouse liver cDNA plasmid library (manufactured by Takara Shuzo Co., Ltd.) as a template. PCR was carried out by a reaction of 94° C., 9 minutes; thereafter 40 cycles of reaction, wherein one cycle comprises a process consisting of 94° C., 0.5 minutes—51° C., 0.5 minutes—72° C., 1 minute; and further an incubation at 72° C. for 7 minutes. By this PCR, a specific amplified DNA fragment of a size of about 70 bp was detected on agarose electrophoresis.

This amplified DNA was collected from the gel, and this DNA was incorporated in pGEM-T easy vector (manufactured by Promega) to construct a recombinant plasmid. An insert DNA fragment of the plasmid was subjected to a nucleotide sequencing. As a result, a partial nucleotide sequence P-1 of this fragment was determined. SEQ ID NO: 6 of Sequence Listing shows the nucleotide sequence of P-1. The sequence is a sequence corresponding to the partial amino acid sequence C-53 of the ceramidase determined in Example 2. It has been confirmed that a part of the desired ceramidase gene could be obtained.

Antisense primers MA1 and MA2 were designed and synthesized on the basis of the nucleotide sequence of P-1. SEQ ID NOs: 7 and 8 of Sequence Listing each show the nucleotide sequences of the primers MA1 and MA2. In addition, sense primers T7in and T7out were designed and synthesized on the basis of the nucleotide sequence of vector pAP3neo used in the construction of the mouse liver cDNA plasmid library. SEQ ID NOs: 9 and 10 of Sequence Listing each show the nucleotide sequences of the primers T7in and T7out. Nested PCR was carried out by using these primers with the mouse liver cDNA plasmid library as a template. A 1st PCR was carried out by using the sense primer T7out and the antisense primer MA2 by a reaction at 94° C., 9 minutes; thereafter 40 cycles of reaction, wherein one cycle comprises a process consisting of 94° C., 0.5 minutes —51° C., 0.5 minutes—72° C., 2 minutes; and further an incubation at 72° C. for 7 minutes. A 2nd PCR was carried out under the same conditions as the 1st PCR except for using the sense primer T7in and the antisense primer MA1 with a reaction mixture of the 1st PCR as a template. Consequently, an amplified DNA fragment of a size of 335 bp was obtained. This DNA fragment was used as a probe for colony hybridization described below.

EXAMPLE 4

Cloning of Ceramidase Gene

A transformant resulting from introducing the mouse liver cDNA plasmid library was inoculated to a nylon filter (trade name Hybond-N$^+$, manufactured by Amersham Pharmacia) on an LB agar medium plate containing 100 µg/ml ampicillin, and about 30000 colonies were formed per one plate of 9.5×13.5 cm to prepare a master filter. A replica of this filter was prepared, and the resulting replica filter was respectively treated for 5 minutes on a filter paper immersed in a 10% SDS solution; 5 minutes on a filter paper immersed in a solution containing 0.5 M NaOH and 1.5 M NaCl (denaturation); 5 minutes on a filter paper immersed in 0.5 M Tris-hydrochloric acid buffer (pH 7.5) containing 3 M NaCl (neutralization); and 5 minutes on a filter paper immersed in 2×SSC solutions. Thereafter, the filter was rinsed with 2×SSC solution. This filter was air-dried, and thereafter DNA was immobilized on a filter by ultraviolet ray irradiation to be used as a filter for colony hybridization.

As the probe for the hybridization, one prepared by $^{32}$P-labeling 0.1 µg equivalent of the amplified DNA fragment obtained in Example 3 by using a DNA labeling kit, Ready To Go (manufactured by Pharmacia) in accordance with the protocol attached to the same kit. The above-mentioned filter was placed in a hybri-bag. The pre-hybridization was carried out at 60° C. for 1 hour in a hybridization solution (composition: 7% PEG6000, 10% SDS solution), and thereafter the above-mentioned labeled probe was added to the mixture so as to have a concentration of 0.006 pmol/ml, and the hybridization was carried out overnight at 60° C. Next the filter was washed three times each for 15 minutes at 60° C. in the washing liquid (2×SSC, 0.1% SDS) previously heated to 60° C. After excess water was removed from the filter, and thereafter the filter was photosensitized on an imaging plate manufactured by Fuji Photo Film for 20 minutes. Thereafter, a signal was detected with BAS1000 imaging analyzer (manufactured by Fuji Photo Film). Subsequently, colonies were collected on a master filter corresponding to a positive signal obtained by these procedures (first screening).

The collected colonies were suspended in an LB medium containing 100 µg/ml ampicillin, and thereafter the suspension was spread over the nylon filter on an LB agar medium plate of 9.5×13.5 cm containing 100 µg/ml ampicillin, and about 200 to about 1000 colonies were formed per one sheet to prepare a master filter. This filter was subjected to screening of a positive clone in the same manner as the first screening, and a third screening was further carried out by the same procedures. As a result of the third screening, the positive clone which was deduced to contain the ceramidase gene could be isolated.

Figure 2:
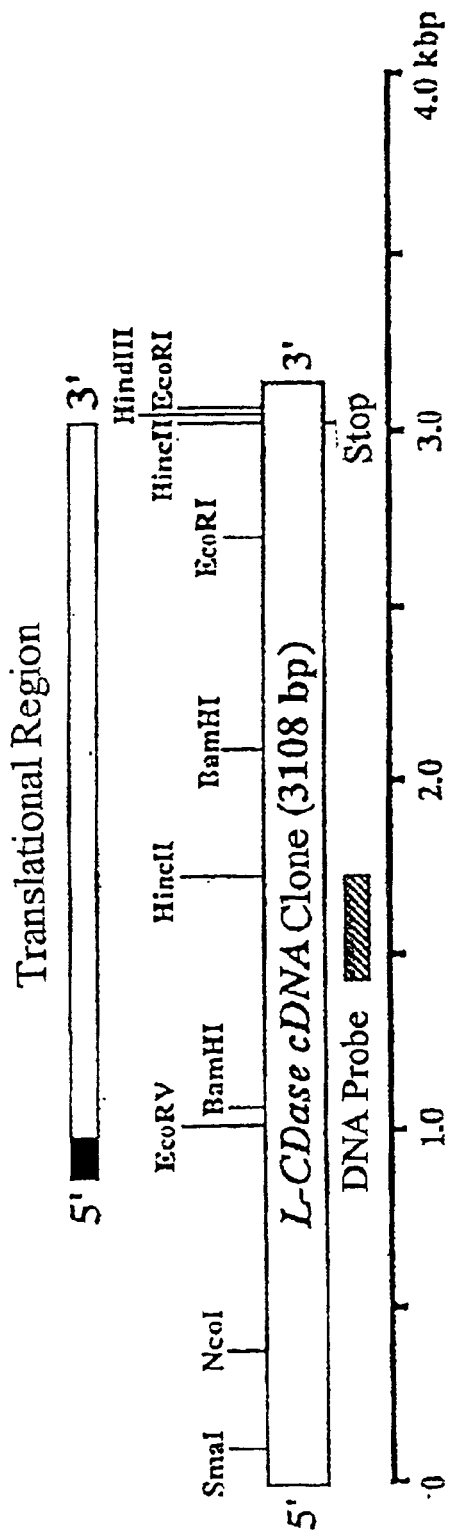
FIG. 2 is a restriction endonuclease map of a DNA fragment comprising the ceramidase gene.

A plasmid was prepared from this positive clone, and this plasmid was named plasmid pLCDase. The plasmid was digested with various kinds of restriction enzymes or a combination of plural restriction enzymes. Thereafter, each of the formed DNA fragments was subcloned, and its nucleotide sequence was analyzed By the above procedures, an entire nucleotide sequence of the DNA fragment inserted in the plasmid pLCDase was determined. The sequence is shown in SEQ ID NO: 11 of Sequence Listing. In addition, the nucleotide sequence of the open reading frame (ORF) found in the sequence and the amino acid sequence of the polypeptide encoded thereby are each shown in SEQ ID NOs: 12 and 13 of Sequence Listing. Further, the restriction enzyme map of the above-mentioned DNA fragment and the position of the open reading frame contained in the DNA fragment are shown in FIG. 2.

As a result of analysis of the nucleotide sequence of the above-mentioned ORF, there were confirmed that the nucleotide sequence comprises a nucleotide sequence encoding a partial amino acid sequence of the ceramidase elucidated by Example 2, and that this ORF encodes ceramidase. In addition, when the amino acid sequence of the ceramidase encoding the ORF was compared with the amino acid sequence of the ceramidase shown in SEQ ID NO: 1 of Sequence Listing, it was shown that the ceramidase purified from the mouse liver lacked the peptide of the N-terminal portion of the polypeptides encoded by the above-mentioned ORF. In other words, it was shown that the ceramidase was converted to a mature enzyme by going through the processing in which its N-terminal portion was removed after the translation. SEQ ID NO: 14 of Sequence Listing shows an amino acid sequence of the mature ceramidase, and SEQ ID NO: 15 of Sequence Listing shows a nucleotide sequence of the mature ceramidase, respectively.

EXAMPLE 5

Expression of Ceramidase Gene

To CHO cells cultured in a 10% FCS-containing α-MEM medium in a dish having a diameter of 35 mm (3×10$^5$ cells/dish) were added 1 µg of the plasmid pLCDase obtained in Example 4 and 5 µl of lipofectamine (manufactured by Life Technologies), thereby transducing a ceramidase gene into CHO cells. The cells were cultured at 37° C. for 24 hours, and thereafter suspended in 100 µl of 10 mM Tris-hydrochloric acid (pH 7.5) containing 0.1% Triton X-100, and the cells were disrupted. The determination of the activity on the ceramidase of which substrate was the above-mentioned C12-NBD-ceramide was made for the resulting solution containing disrupted cells. As a result, it was confirmed that the ceramidase in the cells intensively expressed about 1000 times more than that of the control cells in which pLCDase was not transduced.

Further, the amount of ceramide in the cells was determined in accordance with the method described in *Analytical Biochemistry*, 244, 291–300 (1997). As a result it was confirmed that those pLCDase-transduced cells had a significantly reduced amount of ceramide, as compared to the control cells into which pLCDase was not transduced.

EXAMPLE 6

Cloning of Ceramidase Gene from Mouse Brain

A nitrocellulose membrane (Schleicher & Schuell, PROTRAN BA85 0.45 mm being used with a diameter of 82 mm) was placed on an LB agar medium plate containing 100 µg/ml ampicillin, and the mouse brain cDNA library (LIFE TECHNOLOGIES, SUPERSCRIPT Mouse Brain cDNA Library) was spread on each of 10 plates, so as to be about 200000 colonies per one plate, and cultured at 37° C. for 10 hours. *E. coli* grown on the nitrocellulose membrane was transferred to a nylon membrane [PALL Gelman Laboratory, biodyne A diameter 82 mm (1.2 mm)], and each nylon membrane was placed on an ampicillin plate, and thereafter cultured at 37° C. for 3 hours. The nitrocellulose membrane was stored at 4° C. as a master filter, and the nylon membrane was placed on chloramphenicol plate, and cultured at 37° C. for 16 hours. Colonies were transferred to a fresh nylon membrane from the nylon membrane, and front and back sides of the membrane were each treated for 5 minutes with 1 ml of a denaturation solution (0.5 M NaOH/ 1.5 M NaCl) in a state where each pair of nylon membranes was overlaid. Similarly, the nylon membranes were treated with 1 ml of a neutralization solution [0.5 M Tris-HCl (pH 7.4)/1.5 M NaCl] for 5 minutes. The nylon membrane was peeled of, and the treated membrane was air-dried, and thereafter baked at 80° C. for 2 hours. Thereafter, the baked membrane was shaken with 200 ml of a pre-rinsing liquid [5×SSC/0.5% SDS/1 ml EDTA (pH 8.0)], and disrupted E. coli residues were wiped off, and washed with 2×SCC. The hybridization was carried out with 40 ml of a hybridization solution [0.5 M Church phosphate buffer/7% SDS/1 mM EDTA] at 65° C. for 2 hours, and thereafter the hybridization was carried out at 65° C. for 16 hours in 40 ml of the hybridization solution containing the denatured probe. As the probe, an EcoRI-EcoRI fragment of a size of 2.7 kbp of the plasmid a pAPLCD carrying mouse ceramidase gene was used. After the termination of the hybridization, washing with 100 ml of a washing liquid (40 mM Church phosphate buffer/1% SDS) at 65° C. for 15 minutes was carried out twice. Further, washing with 100 ml of a high stringent washing liquid (0.2×SSC/0.1% SDS) at 65° C. for 15 minutes was carried out. The membrane was air-dried, and thereafter exposed on an IP-plate for 1 hour, and analyzed with BAS 1500. The positive part of the nitrocellulose membrane was cut out in a diameter of about 6 mm, and suspended in 1 ml of the LB medium. Thereafter, a 200 ml sample prepared by diluting the positive part 4000-folds was spread over an ampicillin-containing LB plate, and a 2nd screening was carried out.

Similarly, a 200 ml sample prepared by diluting the positive part 10000-folds was spread over an ampicillin-containing LB plate, to prepare a library. A 3rd screening was carried out by using this library. The isolated clone (pSBCD) was subcloned, and thereafter the nucleotide sequence was determined by a conventional method. This sequence is shown in SEQ ID NO: 16.

In the above-mentioned sequence, an ORF having the identical sequence as the ceramidase gene derived from mouse liver described in Example 4 was found. Incidentally, the sequences of 5' non-translational region and 3' non-translational region were different from those derived from the mouse liver. In addition, the isolated plasmid pSBCD was transduced into CHO cells in the same manner as in Example 5. As a result, it was found that the ceramidase was expressed in the cells.

EXAMPLE 7

Genomic Cloning of Human Ceramidase Gene

Sense primer U1107 having the sequence of SEQ ID NO: 17 of Sequence Listing and antisense primer L1311 having the sequence of SEQ ID NO: 18 of Sequence Listing were synthesized on the basis of the sequence of the ceramidase gene derived from mouse liver determined in Example 4. The sequence of U1107 primer corresponds to a sequence consisting of base nos.: 1107–1130 of SEQ ID NO: 12 of Sequence Listing, and the sequence of L1311 primer corresponds to a nucleotide sequence complementary to a sequence consisting of base nos.: 1311–1334 of SEQ ID NO: 12 of Sequence Listing.

Genomic DNA was purified from human hepatoma cell Huh7 by a conventional method PCR was carried out by using the U1107 primer and the L1311 primer with 625 ng of the resulting genomic DNA as a template. PCR was carried out by a reaction at 94° C., 9 minutes; thereafter 40 cycles of reaction, wherein one cycle comprises a process consisting of 94° C., 0.5 minutes—55° C., 0.5 minutes—72° C., 3 minutes; and further an incubation at 72° C. for 7 minutes. Thereafter, the resulting reaction product was subjected to agarose electrophoresis. As a result, it was confirmed that a DNA fragment of a size of about 2 kbp was amplified by the PCR.

This DNA fragment was collected from the gel by using Sephaglas (manufactured by Pharmacia), and the resulting fragment was incorporated in pGEM-T easy vector (manufactured by Promega) to construct a recombinant plasmid. Next, the nucleotide sequence of the DNA fragment insert of the resulting plasmid was determined. The above-mentioned sequence was a sequence corresponding to 96289–98478 of the Accession No. AC012131 Complement registered in the GenBank Data Base. In addition, the amino acid sequence encoded by the above-mentioned sequence was analyzed. As a result, a region encoding an amino acid sequence showing homology to a region of the amino acid nos.: 370–444 of the amino acid sequence of the ceramidase derived from mouse liver of SEQ ID NO: 4 of Sequence Listing and a region encoding an amino acid sequence showing homology were found.

Incidentally, AC012131 also has homology with the ceramidase gene derived from mouse liver determined in Example 4.

SEQUENCE LISTING FREE TEXT

In the amino acid sequence of SEQ ID NO: 1, each of Xaa in the amino acid numbers: 7, 9 and 13 stands for an unknown amino acid.

SEQ ID NO: 4 is a sequence of synthetic oligonucleotide primers. In the above-mentioned sequence, each of n in the base numbers: 6, 9 and 15 stands for G, A, T or C.

SEQ ID NO: 5 is a sequence of synthetic oligonucleotide primers. In the above-mentioned sequence, each of n in the base numbers: 3, 6 and 15 stands for G, A, T or C.

SEQ ID NO: 7 is a sequence of synthetic oligonucleotide primers.

SEQ ID NO: 8 is a sequence of synthetic oligonucleotide primers.

SEQ ID NO: 9 is a sequence of synthetic oligonucleotide primers.

SEQ ID NO: 10 is a sequence of synthetic oligonucleotide primers.

SEQ ID NO: 11 is a sequence of synthetic oligonucleotide primers.

SEQ ID NO: 17 is a sequence of synthetic oligonucleotide primers.

SEQ ID NO: 18 is a sequence of synthetic oligonucleotide primers.

INDUSTRIAL APPLICABILITY

According to the present invention, a gene encoding a neutral/alkaline ceramidase derived from a mammal is provided, and a genetic engineering method for producing a ceramidase using the gene. Also, the oligonucleotide probe and primer of the pre sent invention are useful for detection of the above-mention and can be applied to studies on in vivo ceramide metabolism. Further, according to the present invention, an antisense nucleic acid (DNA, RNA) of the gene of the present invention is provided. The gene and its antisense nucleic acid are useful in the control of the ceramidase activity and in the regulations of the in vivo ceramide metabolism system. Therefore, a method of regulating an amount of ceramide which can be applied to treatments of diseases caused by the abnormal amount of ceramide is provided.

What is claimed is:

1. An isolated nucleic acid comprising a nucleotide sequence selected from the group consisting of:
   (A) a nucleotide sequence encoding a polypeptide having the amino acid sequence of SEQ ID NO: 14, wherein the polypeptide possesses a ceramidase activity;
   (B) a nucleotide sequence comprising SEQ ID NO: 15, wherein said nucleotide sequence encodes a polypeptide possessing a ceramidase activity; and
   (C) a nucleotide sequence which hybridizes to the complement of the nucleotide sequence of SEQ ID NO: 15 under stringent conditions, wherein said stringent conditions comprise 7% PEG 6000 containing 10% SDS solution at 60° C., and washing three times with 2×SSC containing 0.1% SDS for 15 minutes at 60° C., wherein said nucleotide sequence encodes a polypeptide having activity of hydrolyzing any one of substances selected from the group consisting of (i) N-Lauroylsphinqosine, (ii) N-Palmitoylsphingosine, (iii) N-Stearoylsphingosine, (iv) N-Palmitoylsphinganine, (v) N-Stearoylsphinganine, and (vi) 12-((N-(7-nitrobenz-2-oxa-1,3-diazol-4-yl)amino)dodecanoyl)sphingosine.

2. The nucleic acid according to claim 1, wherein the ceramidase activity of the polypeptide is detected by the following steps:
   (a) incubating an expression product in a reaction mixture comprising 550 pmol of 12-((N-(7-nitrobenz-2-oxa-1,3-diazol-4-yl)amino)dodecanoyl)sphingosine and 1.0% (W/V) sodium cholate in 20 $\mu$l of 25 mM Tris-hydrochloric acid buffer, pH 7.5, at 37° C. for 30 minutes; and
   (b) detecting the formation of a 12-(N-(7-nitrobenz-2-oxa-1,3-diazol-4-yl)amino)dodecanoic acid in the reaction.

3. The nucleic acid according to claim 1 or 2, wherein the polypeptide exhibits at least the following characteristics:
   (i) action of hydrolyzing ceramide to generate sphingoid and a fatty acid;
   (ii) substrate specificity of hydrolyzing N-acylsphingosine, but not acting on galactosylceramide, sulfatide, Galb1-3GalNAcb1-4 (NeuAca2-3)Galb1-4Glcb1-1'Cer (GM1a), and sphingomyelin;
   (iii) optimum pH from 7.0 to 8.0; and
   (iv) incubation in 20 mM Tris-hydrochloric acid buffer, pH 7.5, containing 0.1% polidocanol at 37° C. for 24 hours does not decrease activity of said polypeptide, whereas incubation in 20 mM Tris-hydrochloric acid buffer, pH 7.5, containing 0.1% polidocanol at 60° C. for 1 hour decreases activity of said polypeptide to about 30%.

4. A recombinant DNA comprising the nucleic acid of claim 1.

5. An expression vector comprising the nucleic acid of claim 1 or the recombinant DNA of claim 4.

6. A transformed cell comprising the expression vector of claim 5.

7. A method for producing a polypeptide possessing a ceramidase activity, comprising the steps of culturing the transformed cell of claim 6 under conditions appropriate for expression of the polypeptide, and collecting a polypeptide possessing a ceramidase activity from the resulting culture.

8. An isolated DNA which is complementary to the nucleic acid of claim 1.

9. An isolated RNA which is complementary to the nucleic acid of claim 1.

10. An expression vector comprising the DNA of claim 8.

11. An isolated polypeptide comprising the amino acid sequence of SEQ ID NO: 14, wherein said polypeptide possesses a ceramidase activity.

12. An isolated polypeptide possessing a ceramidase activity, wherein said polypeptide is encoded by the nucleic acid of claim 1.

13. The polypeptide according to claim 11 or 12, wherein the ceramidase activity is detected by the following steps:

(a) incubating an expression product in a reaction mixture comprising 550 pmol of 12-((N-(7-nitrobenz-2-oxa-1, 3-diazol-4-yl)amino)dodecanoyl)sphingosine and 1.0% (W/V) sodium cholate in 20 µl of 25 mM Tris-hydrochloric acid buffer, pH 7.5, at 37° C. for 30 minutes; and (b) detecting the formation of a 12-(N-(7-nitrobenz-2-oxa-1,3-diazol-4-yl)amino)dodecanoic acid in the reaction.

14. A method of controlling an amount of ceramide in a cell, comprising the step of introducing the nucleic acid of claim 1 or a complementary nucleic acid thereof into the cell, thereby controlling the amount of ceramide in the cell.

\* \* \* \* \*

SEQUENCE LISTING

<160> NUMBER OF SEQ ID NOS: 18

<210> SEQ ID NO 1
<211> LENGTH: 21
<212> TYPE: PRT
<213> ORGANISM: Mus sp.
<220> FEATURE:
<221> NAME/KEY: MISC_FEATURE
<222> LOCATION: (1)..(21)
<223> OTHER INFORMATION: any Xaa = any amino acid, unknown, or other

<400> SEQUENCE: 1

Phe Ser Gly Tyr Tyr Ile Xaa Val Xaa Arg Ala Asp Xaa Thr Gly Lys
1               5                   10                  15

Val Asn Asp Ile Asn
            20

<210> SEQ ID NO 2
<211> LENGTH: 10
<212> TYPE: PRT
<213> ORGANISM: Mus sp.
<220> FEATURE:
<221> NAME/KEY: MISC_FEATURE
<222> LOCATION: (1)..(10)
<223> OTHER INFORMATION: any Xaa = any amino acid, unknown, or other

<400> SEQUENCE: 2

Ala Ile Ala Thr Asp Thr Val Ala Xaa Met
1               5                   10

<210> SEQ ID NO 3
<211> LENGTH: 35
<212> TYPE: PRT
<213> ORGANISM: Mus sp.
<220> FEATURE:
<221> NAME/KEY: MISC_FEATURE
<222> LOCATION: (1)..(35)
<223> OTHER INFORMATION: any Xaa = any amino acid, unknown, or other

<400> SEQUENCE: 3

Gly Tyr Leu Pro Gly Gln Gly Pro Phe Val Asn Gly Phe Ala Ser Ser
1               5                   10                  15

Asn Leu Gly Asp Val Ser Pro Asn Ile Leu Gly Pro Xaa Xaa Val Asn
            20                  25                  30

Thr Gly Glu
        35

<210> SEQ ID NO 4
<211> LENGTH: 17
<212> TYPE: DNA
<213> ORGANISM: Artificial Sequence
<220> FEATURE:
<223> OTHER INFORMATION: Synthetic oligonucleotide primer 53-S1 directed
      to gene derived from Mus sp. liver
<221> NAME/KEY: misc_feature
<222> LOCATION: (1)..(17)
<223> OTHER INFORMATION: any n = a, c, g, t, any, unknown, or other

<400> SEQUENCE: 4
carggnccnt tygtngc                                                17

<210> SEQ ID NO 5
<211> LENGTH: 17
<212> TYPE: DNA
<213> ORGANISM: Artificial Sequence

```
<220> FEATURE:
<223> OTHER INFORMATION: Synthetic oligonucleotide primer 53-A3 directed
      to gene derived from Mus sp. liver
<221> NAME/KEY: misc_feature
<222> LOCATION: (1)..(17)
<223> OTHER INFORMATION: any n = a, c, t, g, any, unknown, or other

<400> SEQUENCE: 5
ggnccnagda trttngg                                                  17

<210> SEQ ID NO 6
<211> LENGTH: 38
<212> TYPE: DNA
<213> ORGANISM: Mus sp.

<400> SEQUENCE: 6
gcaggctttg cttcatcaaa tctcggagac gtgtcacc                           38

<210> SEQ ID NO 7
<211> LENGTH: 19
<212> TYPE: DNA
<213> ORGANISM: Artificial Sequence
<220> FEATURE:
<223> OTHER INFORMATION: Synthetic oligonucleotide primer MA1 directed
      to gene derived from Mus sp. liver

<400> SEQUENCE: 7
ttgatgaagc aaagcctgc                                                19

<210> SEQ ID NO 8
<211> LENGTH: 19
<212> TYPE: DNA
<213> ORGANISM: Artificial Sequence
<220> FEATURE:
<223> OTHER INFORMATION: Synthetic oligonucleotide primer MA2 directed
      to gene derived from Mus sp. liver

<400> SEQUENCE: 8
ggtgacacgt ctccgagat                                                19

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer T7in directed
      to gene derived from Mus sp. liver

<400> SEQUENCE: 9
taatacgact cactataggg                                               20

<210> SEQ ID NO 10
<211> LENGTH: 17
<212> TYPE: DNA
<213> ORGANISM: Artificial Sequence
<220> FEATURE:
<223> OTHER INFORMATION: Synthetic oligonucleotide primer T7out directed
      to gene derived from Mus sp. liver

<400> SEQUENCE: 10
tctgctctaa aagctgc                                                  17

<210> SEQ ID NO 11
<211> LENGTH: 3108
<212> TYPE: DNA
<213> ORGANISM: Mus sp.
```

<400> SEQUENCE: 11

```
cctgcgccac ttctctctcc cggctcaatc gcggagcctt ttctctcccc cgtctcgccg      60
ctgccgccat ctccacccct gcctgcccca ggggtctgtg gacgcccggg cagagagcaa     120
gcaccgagct gggcctgctg gagaccggag accagcggcc cgcccgcccg cccgctgcga     180
gcctcctgag cagctccgga acagcttact ttctgtttcc atctcttccg gaccgggttg     240
gcctctccaa aagccacttc tcctaactct tatcaaggtt caaaggctaa aggtctgtac     300
acatgagtgc tggtgtgctt agaggcatcg gtccctttc agctggagtt gcagtacttg     360
tgagtgccat ggaatccaaa ttcggcaaga gatacaatct aaactctcaa ctactccaga     420
ttcaaggttc acctcacttt ctggttacca aggagctttt gcggggccgc tctgacatcc     480
agtagatttg gaaacacatt gagaaatcag cctgagcaac ctgcaaggca caggcacaa     540
gattctgcat ggttatttgc tctcccagga ggtgaacact tgttttgatt cacagagtca     600
gggttgagat gcccagttgt tcctcatctt ggctcagaag aagcacctag gaataaaagc     660
tctaagctgg tattaagtag aatgggctta agtccacta caggaaacaa cagctagtga     720
cagaaatggc aaagcgaacc ttctccacct tggaggcatt cctcattttc cttctggtaa     780
taatgacagt catcacagtg gcccttctca ccctcttgtt tgttaccagt gggaccattg     840
aaaaccacaa agattcagga aatcactggt tttcaaccac tctgggctcc acgacaaccc     900
agccccctcc aattacacag actccaaact tcccttcatt tcggaacttc agtggctact     960
acattggcgt tgggagagcg gattgcacag gacaagtgtc agatatcaat ttgatgggct    1020
atggcaaaaa tggccagaat gcacggggtc tcctcaccag gctgttcagc cgtgctttta    1080
tcttggcgga tccagatggg tcaaatcgaa tggcatttgt gagcgtggaa ctatgtatga    1140
tttcccaacg actgaggttg gaggtcctga agagactaga gagtaaatat ggctctctgt    1200
atcgaagaga caatgttatc ctgagtgcca ttcacacaca ctctggccca gcagggtttt    1260
tccaatatac actctatata ctcgccagcg agggattcag caaccggacc tttcagtaca    1320
tagtctctgg gatcatgaag agcattgata tagctcacac aaatcttaaa ccaggcaaaa    1380
tctttatcaa caaggaaat gttgctaatg tgcagatcaa ccgaagcccc tcctcttacc    1440
ttctgaatcc acagtcagag agagcaaggt attcttcaaa cacagacaag gaaatgctgg    1500
tcttgaaact ggtggatttg aatggagaag acttgggtct tatcagctgg tttgccatcc    1560
accccgtgag catgaacaat agcaaccact tgtgaatag tgacaatatg gctatgcgg     1620
cttacctttt tgagcaagaa aagaacaaag gctatctgcc tggacaggga ccgtttgtag    1680
caggctttgc ttcatcaaat ctcggagacg tgtcacccaa cattcttggc ccgcattgtg    1740
tcaacacagg ggagtcttgt gacaacgaca agagcacctg tcccaacggt gggcctagca    1800
tgtgcatggc cagcggacct ggacaagaca tgtttgagag cacacacatt ataggacgga    1860
tcatctatca gaaggccaag gagctgtatg cctctgcctc ccaggaggtg accggcccag    1920
tgcttgcagc tcaccagtgg gtgaacatga cagatgtgag cgtccagctc aatgccacac    1980
acacagtgaa gacgtgtaaa cctgccctgg gctacagttt tgccgcaggc acaattgatg    2040
gagtttcggg cctcaatatt acacagggaa ctacggaagg ggatccattc tgggacactc    2100
ttcgggacca gctcttggga aaaccatctg aagagattgt agagtgtcag aaacccaaac    2160
caatcctgct tcacagtgga gagctgacga taccacatcc ttggcaacca gatattgttg    2220
atgttcagat tgttaccgtt gggtccttgg ccatagctgc tatccctggg gaattaacaa    2280
ccatgtcggg acgaagattt cgtgaggcaa ttaaaaaaga atttgcactt tatgggatga    2340
```

-continued

```
aggatatgac cgttgttatc gcaggtctaa gcaatgttta tacacattac attaccacat    2400
atgaagaata ccaggctcag cggtacgagg cagcatctac aatctatgga ccacacaccc    2460
tgtctgcata catccaactc ttcagagacc ttgctaaggc aattgctacg dacacagtag    2520
ccaacatgag cagtggtccc gagcctccat tcttcaaaaa tctaatagct tcacttattc    2580
ctaatattgc ggatagagca ccaattggca aacattttgg ggatgtcttg cagccagcaa    2640
aacctgaata cagagtggga gaagtggttg aagttatatt tgtaggcgct aacccaaaga    2700
attcagcaga gaaccagacc catcaaacct tcctcactgt ggagaaatac gaggactctg    2760
tagctgactg gcagataatg tataacgatg cctcctggga gacgaggttt tattggcaca    2820
aaggaatact gggtctgagc aatgcaacaa tatactggca tattccagat actgcctacc    2880
ctggaatcta cagaataaga tattttggac acaatcggaa gcaggaactt ctgaaacccg    2940 ctgtctatact agcatttgaa ggaatttctt ctccttttga agttgtcact acttagtgaa    3000
aagttgacag atattgaaga aaagcttttc tctgtgcaca ttatagagtg aattcacaaa    3060
aaaaaaaaaa aaaaaaaaaa aaaaaaaaaa aaaaaaaaaa aaaaaaaa                3108
```

<210> SEQ ID NO 12
<211> LENGTH: 2271
<212> TYPE: DNA
<213> ORGANISM: Mus sp.

<400> SEQUENCE: 12

```
atggcaaagc gaaccttctc caccttggag gcattcctca ttttccttct ggtaataatg      60
acagtcatca cagtggccct tctcaccctc ttgtttgtta ccagtgggac cattgaaaac     120
cacaaagatt caggaaaatca ctggttttca accactctgg gctccacgac aacccagccc    180
cctccaatta cacagactcc aaacttccct tcatttcgga acttcagtgg ctactacatt     240
ggcgttggga gagcggattg cacaggacaa gtgtcagata tcaatttgat gggctatggc     300
aaaaatggcc agaatgcacg gggtctcctc accaggctgt tcagccgtgc ttttatcttg     360
gcggatccag atgggtcaaa tcgaatgcca tttgtgagcg tggaactatg tatgatttcc     420
caacgactga ggttggaggt cctgaagaga ctagagagta aatatggctc tctgtatcga     480
agagacaatg ttatcctgag tgccattcac acacactctg gcccagcagg ttttttccaa     540
tatacactct atatactcgc cagcgaggga ttcagcaacc ggacctttca gtacatagtc     600
tctgggatca tgaagagcat tgatatagct cacacaaatc ttaaaccagg caaaatcttt     660
atcaacaaag gaaatgttgc taatgtgcag atcaaccgaa gcccctcctc ttaccttctg     720
aatccacagt cagagagagc aaggtattct tcaaacacag acaaggaaat gctggtcttg     780
aaactggtgg atttgaatgg agaagacttg ggtcttatca gctggtttgc catccacccc     840
gtgagcatga acaatagcaa ccactttgtg aatagtgaca atatgggcta tgcggcttac     900 cttttttgagc aagaaaagaa caaaggctat ctgcctggac agggaccgtt tgtagcaggc     960
tttgcttcat caaatctcgg agacgtgtca cccaacattc ttggcccgca ttgtgtcaac    1020
acaggggagt cttgtgacaa cgacaagagc acctgtccca acgtgggcc tagcatgtgc    1080 atggccagcg gacctggaca agacatgttt gagagcacac acattatagg acggatcatc    1140
tatcagaagg ccaaggagct gtatgcctct gcctcccagg aggtgaccgg cccagtgctt    1200
gcagctcacc agtgggtgaa catgacagat gtgagcgtcc agctcaatgc cacacacaca    1260
gtgaagacgt gtaaacctgc cctgggctac agttttgccg caggcacaat tgatggagtt    1320
```

-continued

```
tcgggcctca atattacaca gggaactacg gaagggatc cattctggga cactcttcgg    1380
gaccagctct tgggaaaacc atctgaagag attgtagagt gtcagaaacc caaaccaatc   1440
ctgcttcaca gtggagagct gacgatacca catccttggc aaccagatat tgttgatgtt   1500
cagattgtta ccgttgggtc cttggccata gctgctatcc ctggggaatt aacaaccatg   1560 tcggacgaa  gatttcgtga ggcaattaaa aaagaatttg cactttatgg gatgaaggat    1620
atgaccgttg ttatcgcagg tctaagcaat gtttatacac attacattac cacatatgaa   1680
gaataccagg ctcagcggta cgaggcagca tctacaatct atggaccaca caccctgtct   1740
gcatacatcc aactcttcag agaccttgct aaggcaattg ctacgacac agtagccaac    1800 atgagcagtg gtcccgagcc tccattcttc aaaaatctaa tagcttcact tattcctaat   1860
attgcggata gagcaccaat tggcaaacat tttggggatg tcttgcagcc agcaaaacct   1920
gaatacagag tgggagaagt ggttgaagtt atatttgtag gcgctaaccc aaagaattca   1980
gcagagaacc agaccatca  aaccttcctc actgtggaga atacgagga ctctgtagct    2040 gactggcaga taatgtataa cgatgcctcc tgggagacga ggttttattg cacaaagga    2100 atactgggtc tgagcaatgc aacaatatac tggcatattc cagatactgc ctaccctgga   2160
atctacagaa taagatattt tggacacaat cggaagcagg aacttctgaa acccgctgtc   2220
atactagcat ttgaaggaat ttcttctcct tttgaagttg tcactactta g             2271
```

<210> SEQ ID NO 13
<211> LENGTH: 756
<212> TYPE: PRT
<213> ORGANISM: Mus sp.

<400> SEQUENCE: 13

```
Met Ala Lys Arg Thr Phe Ser Thr Leu Glu Ala Phe Leu Ile Phe Leu
1               5                   10                  15

Leu Val Ile Met Thr Val Ile Thr Val Ala Leu Leu Thr Leu Leu Phe
            20                  25                  30

Val Thr Ser Gly Thr Ile Glu Asn His Lys Asp Ser Gly Asn His Trp
        35                  40                  45

Phe Ser Thr Thr Leu Gly Ser Thr Thr Gln Pro Pro Ile Thr
    50                  55                  60

Gln Thr Pro Asn Phe Pro Ser Phe Arg Asn Phe Ser Gly Tyr Tyr Ile
65                  70                  75                  80

Gly Val Gly Arg Ala Asp Cys Thr Gly Gln Val Ser Asp Ile Asn Leu
                85                  90                  95

Met Gly Tyr Gly Lys Asn Gly Gln Asn Ala Arg Gly Leu Leu Thr Arg
            100                 105                 110

Leu Phe Ser Arg Ala Phe Ile Leu Ala Asp Pro Asp Gly Ser Asn Arg
        115                 120                 125

Met Ala Phe Val Ser Val Glu Leu Cys Met Ile Ser Gln Arg Leu Arg
    130                 135                 140

Leu Glu Val Leu Lys Arg Leu Glu Ser Lys Tyr Gly Ser Leu Tyr Arg
145                 150                 155                 160

Arg Asp Asn Val Ile Leu Ser Ala Ile His Thr His Ser Gly Pro Ala
                165                 170                 175

Gly Phe Phe Gln Tyr Thr Leu Tyr Ile Leu Ala Ser Glu Gly Phe Ser
            180                 185                 190

Asn Arg Thr Phe Gln Tyr Ile Val Ser Gly Ile Met Lys Ser Ile Asp
        195                 200                 205
```

-continued

```
Ile Ala His Thr Asn Leu Lys Pro Gly Lys Ile Phe Ile Asn Lys Gly
210                 215                 220

Asn Val Ala Asn Val Gln Ile Asn Arg Ser Pro Ser Ser Tyr Leu Leu
225                 230                 235                 240

Asn Pro Gln Ser Glu Arg Ala Arg Tyr Ser Ser Asn Thr Asp Lys Glu
                245                 250                 255

Met Leu Val Leu Lys Leu Val Asp Leu Asn Gly Glu Asp Leu Gly Leu
                260                 265                 270

Ile Ser Trp Phe Ala Ile His Pro Val Ser Met Asn Asn Ser Asn His
        275                 280                 285

Phe Val Asn Ser Asp Asn Met Gly Tyr Ala Ala Tyr Leu Phe Glu Gln
290                 295                 300

Glu Lys Asn Lys Gly Tyr Leu Pro Gly Gln Gly Pro Phe Val Ala Gly
305                 310                 315                 320

Phe Ala Ser Ser Asn Leu Gly Asp Val Ser Pro Asn Ile Leu Gly Pro
                325                 330                 335

His Cys Val Asn Thr Gly Glu Ser Cys Asp Asn Asp Lys Ser Thr Cys
                340                 345                 350

Pro Asn Gly Gly Pro Ser Met Cys Met Ala Ser Gly Pro Gly Gln Asp
                355                 360                 365

Met Phe Glu Ser Thr His Ile Ile Gly Arg Ile Ile Tyr Gln Lys Ala
370                 375                 380

Lys Glu Leu Tyr Ala Ser Ala Ser Gln Glu Val Thr Gly Pro Val Leu
385                 390                 395                 400

Ala Ala His Gln Trp Val Asn Met Thr Asp Val Ser Val Gln Leu Asn
                405                 410                 415

Ala Thr His Thr Val Lys Thr Cys Lys Pro Ala Leu Gly Tyr Ser Phe
                420                 425                 430

Ala Ala Gly Thr Ile Asp Gly Val Ser Gly Leu Asn Ile Thr Gln Gly
                435                 440                 445

Thr Thr Glu Gly Asp Pro Phe Trp Asp Thr Leu Arg Asp Gln Leu Leu
450                 455                 460

Gly Lys Pro Ser Glu Glu Ile Val Glu Cys Gln Lys Pro Lys Pro Ile
465                 470                 475                 480

Leu Leu His Ser Gly Glu Leu Thr Ile Pro His Pro Trp Gln Pro Asp
                485                 490                 495

Ile Val Asp Val Gln Ile Val Thr Val Gly Ser Leu Ala Ile Ala Ala
                500                 505                 510

Ile Pro Gly Glu Leu Thr Thr Met Ser Gly Arg Arg Phe Arg Glu Ala
                515                 520                 525

Ile Lys Lys Glu Phe Ala Leu Tyr Gly Met Lys Asp Met Thr Val Val
                530                 535                 540

Ile Ala Gly Leu Ser Asn Val Tyr Thr His Tyr Ile Thr Thr Tyr Glu
545                 550                 555                 560

Glu Tyr Gln Ala Gln Arg Tyr Glu Ala Ala Ser Thr Ile Tyr Gly Pro
                565                 570                 575

His Thr Leu Ser Ala Tyr Ile Gln Leu Phe Arg Asp Leu Ala Lys Ala
                580                 585                 590

Ile Ala Thr Asp Thr Val Ala Asn Met Ser Ser Gly Pro Glu Pro Pro
                595                 600                 605

Phe Phe Lys Asn Leu Ile Ala Ser Leu Ile Pro Asn Ile Ala Asp Arg
610                 615                 620

Ala Pro Ile Gly Lys His Phe Gly Asp Val Leu Gln Pro Ala Lys Pro
```

```
                625                 630                 635                 640
Glu Tyr Arg Val Gly Glu Val Val Glu Val Ile Phe Val Gly Ala Asn
                    645                 650                 655

Pro Lys Asn Ser Ala Glu Asn Gln Thr His Gln Thr Phe Leu Thr Val
                    660                 665                 670

Glu Lys Tyr Glu Asp Ser Val Ala Asp Trp Gln Ile Met Tyr Asn Asp
                    675                 680                 685

Ala Ser Trp Glu Thr Arg Phe Tyr Trp His Lys Gly Ile Leu Gly Leu
                690                 695                 700

Ser Asn Ala Thr Ile Tyr Trp His Ile Pro Asp Thr Ala Tyr Pro Gly
705                 710                 715                 720

Ile Tyr Arg Ile Arg Tyr Phe Gly His Asn Arg Lys Gln Glu Leu Leu
                    725                 730                 735

Lys Pro Ala Val Ile Leu Ala Phe Glu Gly Ile Ser Ser Pro Phe Glu
                    740                 745                 750

Val Val Thr Thr
            755

<210> SEQ ID NO 14
<211> LENGTH: 682
<212> TYPE: PRT
<213> ORGANISM: Mus sp.

<400> SEQUENCE: 14

Phe Ser Gly Tyr Tyr Ile Gly Val Gly Arg Ala Asp Cys Thr Gly Gln
1               5                   10                  15

Val Ser Asp Ile Asn Leu Met Gly Tyr Gly Lys Asn Gly Gln Asn Ala
                20                  25                  30

Arg Gly Leu Leu Thr Arg Leu Phe Ser Arg Ala Phe Ile Leu Ala Asp
            35                  40                  45

Pro Asp Gly Ser Asn Arg Met Ala Phe Val Ser Val Glu Leu Cys Met
        50                  55                  60

Ile Ser Gln Arg Leu Arg Leu Glu Val Leu Lys Arg Leu Glu Ser Lys
65                  70                  75                  80

Tyr Gly Ser Leu Tyr Arg Arg Asp Asn Val Ile Leu Ser Ala Ile His
                85                  90                  95

Thr His Ser Gly Pro Ala Gly Phe Phe Gln Tyr Thr Leu Tyr Ile Leu
                100                 105                 110

Ala Ser Glu Gly Phe Ser Asn Arg Thr Phe Gln Tyr Ile Val Ser Gly
            115                 120                 125

Ile Met Lys Ser Ile Asp Ile Ala His Thr Asn Leu Lys Pro Gly Lys
        130                 135                 140

Ile Phe Ile Asn Lys Gly Asn Val Ala Asn Val Gln Ile Asn Arg Ser
145                 150                 155                 160

Pro Ser Ser Tyr Leu Leu Asn Pro Gln Ser Glu Arg Ala Arg Tyr Ser
                165                 170                 175

Ser Asn Thr Asp Lys Glu Met Leu Val Leu Lys Leu Val Asp Leu Asn
                180                 185                 190

Gly Glu Asp Leu Gly Leu Ile Ser Trp Phe Ala Ile His Pro Val Ser
            195                 200                 205

Met Asn Asn Ser Asn His Phe Val Asn Ser Asp Asn Met Gly Tyr Ala
        210                 215                 220

Ala Tyr Leu Phe Glu Gln Glu Lys Asn Lys Gly Tyr Leu Pro Gly Gln
225                 230                 235                 240
```

-continued

```
Gly Pro Phe Val Ala Gly Phe Ala Ser Ser Asn Leu Gly Asp Val Ser
            245                 250                 255

Pro Asn Ile Leu Gly Pro His Cys Val Asn Thr Gly Glu Ser Cys Asp
        260                 265                 270

Asn Asp Lys Ser Thr Cys Pro Asn Gly Pro Ser Met Cys Met Ala
    275                 280                 285

Ser Gly Pro Gly Gln Asp Met Phe Glu Ser Thr His Ile Ile Gly Arg
290                 295                 300

Ile Ile Tyr Gln Lys Ala Lys Glu Leu Tyr Ala Ser Ala Ser Gln Glu
305                 310                 315                 320

Val Thr Gly Pro Val Leu Ala Ala His Gln Trp Val Asn Met Thr Asp
                325                 330                 335

Val Ser Val Gln Leu Asn Ala Thr His Thr Val Lys Thr Cys Lys Pro
            340                 345                 350

Ala Leu Gly Tyr Ser Phe Ala Ala Gly Thr Ile Asp Gly Val Ser Gly
        355                 360                 365

Leu Asn Ile Thr Gln Gly Thr Thr Glu Gly Asp Pro Phe Trp Asp Thr
370                 375                 380

Leu Arg Asp Gln Leu Leu Gly Lys Pro Ser Glu Glu Ile Val Glu Cys
385                 390                 395                 400

Gln Lys Pro Lys Pro Ile Leu Leu His Ser Gly Glu Leu Thr Ile Pro
                405                 410                 415

His Pro Trp Gln Pro Asp Ile Val Asp Val Gln Ile Val Thr Val Gly
            420                 425                 430

Ser Leu Ala Ile Ala Ala Ile Pro Gly Glu Leu Thr Thr Met Ser Gly
        435                 440                 445

Arg Arg Phe Arg Glu Ala Ile Lys Lys Glu Phe Ala Leu Tyr Gly Met
450                 455                 460

Lys Asp Met Thr Val Val Ile Ala Gly Leu Ser Asn Val Tyr Thr His
465                 470                 475                 480

Tyr Ile Thr Thr Tyr Glu Glu Tyr Gln Ala Gln Arg Tyr Glu Ala Ala
                485                 490                 495

Ser Thr Ile Tyr Gly Pro His Thr Leu Ser Ala Tyr Ile Gln Leu Phe
            500                 505                 510

Arg Asp Leu Ala Lys Ala Ile Ala Thr Asp Thr Val Ala Asn Met Ser
        515                 520                 525

Ser Gly Pro Glu Pro Pro Phe Phe Lys Asn Leu Ile Ala Ser Leu Ile
530                 535                 540

Pro Asn Ile Ala Asp Arg Ala Pro Ile Gly Lys His Phe Gly Asp Val
545                 550                 555                 560

Leu Gln Pro Ala Lys Pro Glu Tyr Arg Val Gly Glu Val Val Glu Val
                565                 570                 575

Ile Phe Val Gly Ala Asn Pro Lys Asn Ser Ala Glu Asn Gln Thr His
            580                 585                 590

Gln Thr Phe Leu Thr Val Glu Lys Tyr Glu Asp Ser Val Ala Asp Trp
        595                 600                 605

Gln Ile Met Tyr Asn Asp Ala Ser Trp Glu Thr Arg Phe Tyr Trp His
610                 615                 620

Lys Gly Ile Leu Gly Leu Ser Asn Ala Thr Ile Tyr Trp His Ile Pro
625                 630                 635                 640

Asp Thr Ala Tyr Pro Gly Ile Tyr Arg Ile Arg Tyr Phe Gly His Asn
                645                 650                 655

Arg Lys Gln Glu Leu Leu Lys Pro Ala Val Ile Leu Ala Phe Glu Gly
```

|     |     |     | 660 |     |     |     | 665 |     |     |     | 670 |
| --- | --- | --- | --- | --- | --- | --- | --- | --- | --- | --- | --- |
| Ile | Ser | Ser | Pro | Phe | Glu | Val | Val | Thr | Thr |     |     |
|     |     |     | 675 |     |     |     | 680 |     |     |     |     |

<210> SEQ ID NO 15
<211> LENGTH: 2049
<212> TYPE: DNA
<213> ORGANISM: Mus sp.

<400> SEQUENCE: 15

```
ttcagtggct actacattgg cgttgggaga gcggattgca caggacaagt gtcagatatc      60
aatttgatgg gctatggcaa aaatggccag aatgcacggg gtctcctcac caggctgttc     120
agccgtgctt ttatcttggc ggatccagat gggtcaaatc gaatggcatt tgtgagcgtg     180
gaactatgta tgatttccca acgactgagg ttggaggtcc tgaagagact agagagtaaa     240
tatggctctc tgtatcgaag agacaatgtt atcctgagtg ccattcacac acactctggc     300
ccagcaggt tttccaata tacactctat atactcgcca gcgagggatt cagcaaccgg     360
acctttcagt acatagtctc tgggatcatg aagagcattg atatagctca cacaaatctt     420
aaaccaggca aaatctttat caacaaagga atgttgcta atgtgcagat caaccgaagc     480
ccctcctctt accttctgaa tccacagtca gagagagcaa ggtattcttc aaacacagac     540
aaggaaatgc tggtcttgaa actggtggat ttgaatggag aagacttggg tcttatcagc     600
tggtttgcca tccaccccgt gagcatgaac aatagcaacc actttgtgaa tagtgacaat     660
atgggctatg cggcttacct ttttgagcaa gaaaagaaca aaggctatct gcctggacag     720
ggaccgtttg tagcaggctt tgcttcatca aatctcggag acgtgtcacc caacattctt     780
ggcccgcatt gtgtcaacac aggggagtct tgtgacaacg acaagagcac ctgtcccaac     840
ggtgggccta gcatgtgcat ggccagcgga cctggacaag acatgtttga gagcacacac     900
attataggac ggatcatcta tcagaaggcc aaggagctgt atgcctctgc ctcccaggag     960
gtgaccggcc cagtgcttgc agctcaccag tgggtgaaca tgacagatgt gagcgtccag    1020
ctcaatgcca cacacacagt gaagacgtgt aaacctgccc tgggctacag ttttgccgca    1080
ggcacaattg atggagtttc gggcctcaat attacacagg gaactacgga aggggatcca    1140
ttctgggaca ctcttcggga ccagctcttg gaaaaccat ctgaagagat tgtagagtgt    1200
cagaaaccca accaatcct gcttcacagt ggagagctga cgataccaca tccttggcaa    1260
ccagatattg ttgatgttca gattgttacc gttgggtcct tggccatagc tgctatccct    1320
ggggaattaa caaccatgtc gggacgaaga tttcgtgagg caattaaaaa agaatttgca    1380
ctttatggga tgaaggatat gaccgttgtt atcgcaggtc taagcaatgt ttatacacat    1440
tacattacca catatgaaga ataccaggct cagcggtacg aggcagcatc tacaatctat    1500
ggaccacaca ccctgtctgc atacatccaa ctcttcagag accttgctaa ggcaattgct    1560
acggacacag tagccaacat gagcagtggt cccgagcctc cattcttcaa aaatctaata    1620
gcttcactta ttcctaatat tgcggataga gcaccaattg caaacatttt tggggatgtc    1680
ttgcagccag caaaacctga atacagagtg ggagaagtgg ttgaagttat atttgtaggc    1740
gctaacccaa agaattcagc agagaaccag acccatcaaa ccttcctcac tgtggagaaa    1800
tacgaggact ctgtagctga ctggcagata atgtataacg atgcctcctg ggagacgagg    1860
ttttattggc acaaaggaat actgggtctg agcaatgcaa caatatactg gcatattcca    1920
gatactgcct accctggaat ctacagaata agatattttg gacacaatcg gaagcaggaa    1980
```

-continued

| | |
|---|---|
| cttctgaaac ccgctgtcat actagcattt gaaggaattt cttctccttt tgaagttgtc | 2040 |
| actacttag | 2049 |

<210> SEQ ID NO 16
<211> LENGTH: 4835
<212> TYPE: DNA
<213> ORGANISM: Mus sp.

<400> SEQUENCE: 16

| | |
|---|---|
| cctgcagcgg tgttctgaag agccgggcag aggatacaca agcatcccag caggcactct | 60 |
| ggtttgcccg tgaacgatag atatgcgggg gtttgaatga gcagctgcag cagcgggttt | 120 |
| gggtctgtac acatgagtgc tggtgtgctt agaggcatcg ggtcccttc agctggagtt | 180 |
| gcagtacttg tgagtgccat atttggaaac acattgagaa atcagcctga gcaacctgca | 240 |
| aggcacaagg cacaagattc tgcatggtta tttgctctcc caggaggtga acacttgttt | 300 |
| tgattaacag agtcagggtt gagatgccca gttgttcctc atcttggctc agaagaagca | 360 |
| cctaggaata aaagctctaa gctggtatta agtagaatgg gcttaaagtc cactacagga | 420 |
| aacaacagct agtgacagaa atggcaaagc gaaccttctc caccttggag gcattcctca | 480 |
| ttttccttct ggtaataatg acagtcatca cagtggccct tctcacccte ttgtttgtta | 540 |
| ccagtgggac cattgaaaac cacaaagatt caggaaatca ctggttttca accactctgg | 600 |
| gctccacgac aacccagccc cctccaatta cacagactcc aaacttccct tcatttcgga | 660 |
| acttcagtgg ctactacatt ggcgttggga gagcagattg cacaggacaa gtgtcagata | 720 |
| tcaatttgat gggctatggc aaaaatggcc agaatgcacg gggtctcctc accaggctgt | 780 |
| tcagccgtgc ttttatcttg gcggatccag atgggtcaaa tcgaatggca tttgtgagcg | 840 |
| tggaactatg tatgatttcc caacgactga ggttggaggt cctgaagaga ctagagagta | 900 |
| aatatggctc tctgtatcga agagacaatg ttatcctgag tgccattcac acacactctg | 960 |
| gcccagcagg ttttttccaa tatacactct atatactcgc cagcgaggga ttcagcaacc | 1020 |
| ggacctttca gtacatagtc tctgggatca tgaagagcat tgatatagct cacacaaatc | 1080 |
| ttaaaccagg caaaatcttt atcaacaaag gaaatgttgc taatgtgcag atcaaccgaa | 1140 |
| gcccctcctc ttaccttctg aatccacagt cagagagagc aagtattct tcaaacacag | 1200 |
| acaaggaaat gctggtcttg aaactggtgg atttgaatgg agaagacttg ggtcttatca | 1260 |
| gctggtttgc catccacccc gtgagcatga acaatagcaa ccactttgtg aatagtgaca | 1320 |
| atatgggcta tgcggcttac cttttttgagc aagaaaagaa caaaggctat ctgcctggac | 1380 |
| agggaccgtt tgtagcaggc tttgcttcat caaatctcgg agacgtgtca cccaacattc | 1440 |
| ttggcccgca ttgtgtcaac acaggggagt cttgtgacac cgacaagagc acctgtccca | 1500 |
| acggtgggcc tagcatgtgc atggccagcg gacctggaca agacatgttt gagagcacac | 1560 |
| acattatagg acggatcatc tatcagaagg ccaaggagct gtatgcctct gcctcccagg | 1620 |
| aggtgaccgg cccagtgctt gcagctcacc agtgggtgaa catgacagat gtgagcgtcc | 1680 |
| agctcaatgc cacacacaca gtgaagacgt gtaaacctgc cctgggctac agttttgccg | 1740 |
| caggcacaat tgatggagtt tcgggcctca atattacaca gggaactacg gaagggatc | 1800 |
| cattctggga cactcttcgg gaccagctct tgggaaaacc atctgaagag attgtagagt | 1860 |
| gtcagaaacc caaaccaatc ctgcttcaca gtggagagct gacgatacca catccttggc | 1920 |
| aaccagatat tgttgatgtt cagattgtta ccgttgggtc cttggccata gctgctatcc | 1980 |
| ctggggaatt aacaaccatg tcgggacgaa gatttcgtga ggcaattaaa aaagaatttg | 2040 |

-continued

```
cactttatgg gatgaaggat atgaccgttg ttatcgcagg tctaagcaat gtttatacac    2100
attacattac cacatatgaa gaataccagg ctcagcggta cgaggcagca tctacaatct    2160
atggaccaca caccctgtct gcatacatcc aactcttcag agaccttgct aaggcaattg    2220
ctacggacac agtagccaac atgagcagtg gtcccgagcc tccattcttc aaaaatctaa    2280
tagcttcact tattcctaat attgcggata gagcaccaat tggcaaacat tttggggatg    2340
tcttgcagcc agcaaaacct gaatacagag tgggagaagt ggttgaagtt atatttgtag    2400
gcgctaaccc aaagaattca gcagagaacc agacccatca aaccttcctc actgtggaga    2460
aatacgagga ctctgtagct gactggcaga taatgtataa cgatgcctcc tgggagacga    2520
ggttttattg gcacaaagga atactgggtc tgagcaatgc aacaatatac tggcatattc    2580
cagatactgc ctaccctgga atctacagaa taagatattt tggacacaat cggaagcagg    2640
aacttctgaa acccgctgtc atactagcat ttgaaggaat tcttctcct  tttgaagttg    2700
tcactactta gtgaaaagtt gacagatatt gaagaaaagc ttttctctgt gcacattata    2760
gagtgaattc acacaaatgt gaactgccag tttaatttct gtaattgtct ctgtttgggg    2820
gacaggtcat ttattgctaa tgggacagag gtatgtgttt gtgttgttgt atgattatga    2880
gtatgcatgc taacaggaag agagagggag gagggaggga ggagggggag ggagggaaga    2940
aaggagggag agagagagtg agagaatgag agagagagtg agagagaaag agttattagt    3000
gagcaagaga atatgagaga agggccactg acaaccaaat accttgtgat ctttatccta    3060
aagcatgatt ttccttgaag ctctgtggtt gtttaagaga taattccctc taatatgaaa    3120
tccctgaaat ataatgacag tatttgaaga tatgtgaata atgtttatcc tatttatta    3180
tagacttact aaatgagaac actagagaac tttctagaag tcctctagaa tgatacttga    3240
ttttacagag aggaaaagga gctttgattc tctttaggtt agaataaggt tagtatattt    3300
ttccctagtc atatttacaa aataccatgt aactttacta caaatatttg agcccagcta    3360
aaatatcccc agaaaattag cataccagtt ttgttttgtt ttattttgtt tttgcatcca    3420
aacaagcata gtccttctga taagtcactt tagaatggat ctgcctggct cagggttatt    3480
gttcatgctc agatcatttc cgcaattacc tccagagtcc aactatgcga atgtcacttg    3540
cagtgctttg atttatgcct tgtattcctc aaagtgtcct tatcctgcta agtcacacct    3600
cttcctccca gcatttactc taaatgattt ttaatgtttt cgccaatcaa atgtacctca    3660
cattacaaag ctttgccttg aatgtagatt tttaaaacaa aagtgttaag gctggaaatg    3720
tagttatcaa agaggaagtt ttaaatgtat ctgttctttt atcagctact ccctccctca    3780
tggctccctt gaatcactga atagttattt aaacccacat atccaatatg gtactcattc    3840
ctgggtcttc acaattacag acatcatatc gaaatgattg ggctgacaat tcctttgaag    3900
gacaaagtaa atatttaatg agaaatatag attctggaga ggcatttgaa atcacaaat    3960
gttacgcctc catttcctgt tttccaggct gggtgttctg atttgggagg aaagcagccc    4020
caaataattt ttaaatatga atctgaaaat aatgttttag aaattatgat ctcgacagtc    4080
taattaatga gaattgtctg aaagtcctag ctgcatttaa aattatgtaa gttaactaaa    4140
gccaattttt gaaccccagt cataattgtg taggtaggta aaaagagcat tttaggagga    4200
aaccgaactt catttcaaga ctgaatctgt tttaaaagaa caatagtggt aaggtaaatc    4260
ttcatttatt tccctatggt ttacctattt aaacatcgaa gattgaatca aaaggcacct    4320
ggagcatatt ttggtaactc catttcccac ttggtagttc tatggatgct aactgctgaa    4380
```

```
gaataaactg atcgggattt tcaaggggttg tgaacatgtc tcctgatggg aataccgtat      4440
taagtataaa ggttcaaaat agttgatctc aaaactatac acacacacac aatatatata      4500
tatatacaca cacacacatg tacacacaca cacacatgca catacacatg gtattgttta      4560
aaatttattt ctcatgactt agaacaatat aaggattata caaggattca tttcccacca      4620
tcattcctcc cagtgaagct tttctcaaag tctgagtagg agtttctcct ttctcactgg      4680
taactatccc acagtggcca ttacatcact agtaatcggt gtgcccagcc ctgcatggaa      4740
ataaatcaca gaaacataat ttcccagtag acttagtctc ttcaagcctg tgtgcttcta      4800
gtgtataaaa tctgtaaaaa aaaaaaaaaa aaaaa                                 4835

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide sense primer U1107
      directed to gene derived from Mus sp. liver

<400> SEQUENCE: 17
gtttgagagc acacacatta tagg                                               24

<210> SEQ ID NO 18
<211> LENGTH: 24
<212> TYPE: DNA
<213> ORGANISM: Artificial Sequence
<220> FEATURE:
<223> OTHER INFORMATION: Synthetic oligonucleotide antisense primer
      L1311 directed to gene derived from Mus sp. liver

<400> SEQUENCE: 18
atattgaggc ccgaaactcc atca                                               24
```